United States Patent
Morley et al.

(10) Patent No.: US 6,840,938 B1
(45) Date of Patent: Jan. 11, 2005

(54) BIPOLAR CAUTERIZING INSTRUMENT

(75) Inventors: Tracey A. Morley, Sunnyvale, CA (US); Daniel T. Wallace, Redwood City, CA (US); Christopher W. Maurer, Sandy Hook, CT (US)

(73) Assignee: Intuitive Surgical, Inc., Mountain View, CA (US)

( * ) Notice: Subject to any disclaimer, the term of this patent is extended or adjusted under 35 U.S.C. 154(b) by 19 days.

(21) Appl. No.: 10/032,317

(22) Filed: Dec. 21, 2001

Related U.S. Application Data

(60) Provisional application No. 60/258,750, filed on Dec. 29, 2000.

(51) Int. Cl.[7] ............................................. A61B 18/14
(52) U.S. Cl. ............................ 606/51; 606/50; 901/29
(58) Field of Search ................. 606/50–52, 205–211; 901/15, 28, 29, 30

(56) References Cited

U.S. PATENT DOCUMENTS

| | | |
|---|---|---|
| 4,281,447 A | 8/1981 | Miller et al. |
| 4,332,066 A | 6/1982 | Hailey et al. |
| 4,486,928 A | 12/1984 | Tucker et al. |
| 4,500,065 A | 2/1985 | Hennekes et al. |
| 4,512,709 A | 4/1985 | Hennekes et al. |
| 4,706,372 A | 11/1987 | Ferrero et al. |
| 4,710,093 A | 12/1987 | Zimmer et al. |
| 4,793,053 A | 12/1988 | Zuccaro et al. |
| 4,809,747 A | 3/1989 | Choly et al. |
| 4,830,569 A | 5/1989 | Jannborg |
| 4,832,198 A | 5/1989 | Alikhan |
| 4,943,939 A | 7/1990 | Hoover |
| 4,979,949 A | 12/1990 | Matsen, III et al. |
| 4,996,975 A | 3/1991 | Nakamura |
| 5,018,266 A | 5/1991 | Hutchinson et al. |
| 5,078,140 A | 1/1992 | Kwoh |
| 5,143,453 A | 9/1992 | Weynant |
| 5,154,717 A | 10/1992 | Matsen, III et al. |
| 5,174,300 A | 12/1992 | Bales et al. |
| 5,217,003 A | 6/1993 | Wilk |
| 5,221,283 A | 6/1993 | Chang |
| 5,236,432 A | 8/1993 | Matsen, III et al. |
| 5,255,429 A | 10/1993 | Nishi et al. |
| 5,257,998 A | 11/1993 | Ota et al. |
| 5,271,384 A | 12/1993 | McEwen et al. |
| 5,294,209 A | 3/1994 | Naka et al. |
| 5,305,203 A | 4/1994 | Raab |
| 5,312,212 A | 5/1994 | Naumec |
| 5,313,935 A | 5/1994 | Kortenbach et al. |
| 5,343,385 A | 8/1994 | Joskowicz et al. |
| 5,354,314 A | 10/1994 | Hardy et al. |

(List continued on next page.)

FOREIGN PATENT DOCUMENTS

| | | |
|---|---|---|
| WO | WO 93/13916 | 7/1993 |
| WO | WO 94/26167 | 11/1994 |
| WO | WO 95/16396 | 6/1995 |
| WO | WO 95/30964 | 11/1995 |
| WO | WO 96/39944 | 12/1996 |

*Primary Examiner*—Roy D. Gibson
*Assistant Examiner*—Aaron Roane
(74) *Attorney, Agent, or Firm*—Townsend and Townsend and Crew LLP

(57) ABSTRACT

A bipolar surgical instrument that includes opposing grips that can engage the tissue. A current is delivered from an electrosurgical power source to electrodes disposed on the grips to cauterize the tissue. The electrode configurations provide efficient cauterization of the tissue. In some embodiments, the positive and negative electrodes will be offset from each other to prevent shorting and to provide a thin line of coagulation heating to the gripped tissue. In some embodiments the electrodes are removably coupled to the grips through nonconductive sleeves. In some embodiments, the first electrode is disposed in a groove and the second electrode is disposed on a boss.

30 Claims, 19 Drawing Sheets

U.S. PATENT DOCUMENTS

| | | | | |
|---|---|---|---|---|
| 5,355,743 | A | 10/1994 | Tesar | |
| 5,359,993 | A | 11/1994 | Slater et al. | |
| 5,372,147 | A | 12/1994 | Lathrop, Jr. et al. | |
| 5,397,323 | A | 3/1995 | Taylor | |
| 5,399,951 | A | 3/1995 | Lavallee et al. | |
| 5,400,267 | A | 3/1995 | Denen et al. | |
| 5,402,801 | A | 4/1995 | Taylor | |
| 5,403,319 | A | 4/1995 | Matsen, III et al. | |
| 5,417,210 | A | 5/1995 | Funda et al. | |
| 5,427,097 | A | 6/1995 | Depp | |
| 5,451,368 | A | 9/1995 | Jacob | |
| 5,649,956 | A | 7/1997 | Jensen et al. | |
| 5,697,939 | A | 12/1997 | Kubota et al. | |
| 5,762,458 | A | 6/1998 | Wang et al. | |
| 5,792,135 | A | 8/1998 | Madhani et al. | |
| 5,800,423 | A | 9/1998 | Jensen | |
| 6,083,222 | A * | 7/2000 | Klein et al. | 606/41 |
| 6,132,368 | A * | 10/2000 | Cooper | 600/102 |
| 6,152,923 | A * | 11/2000 | Ryan | 606/51 |
| 6,162,220 | A * | 12/2000 | Nezhat | 606/48 |
| 6,206,903 | B1 * | 3/2001 | Ramans | 606/205 |
| 6,331,181 | B1 | 12/2001 | Tierney et al. | |
| 6,394,998 | B1 * | 5/2002 | Wallace et al. | 606/1 |
| 6,458,130 | B1 * | 10/2002 | Frazier et al. | 606/51 |
| 6,511,480 | B1 * | 1/2003 | Tetzlaff et al. | 606/51 |

* cited by examiner

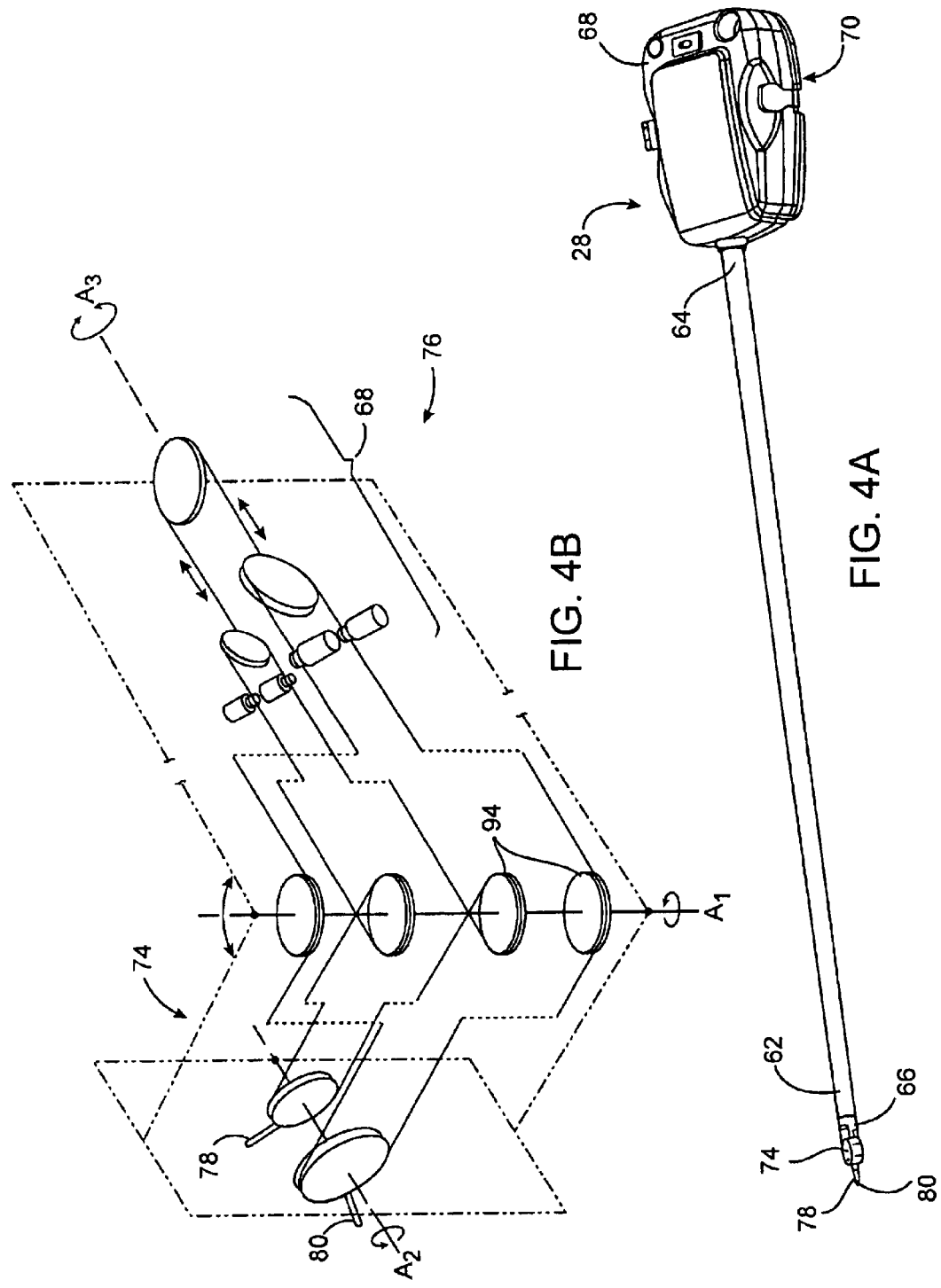

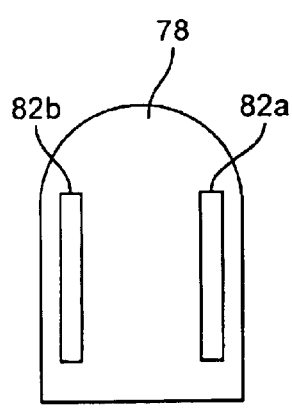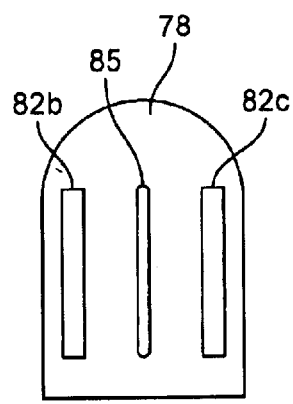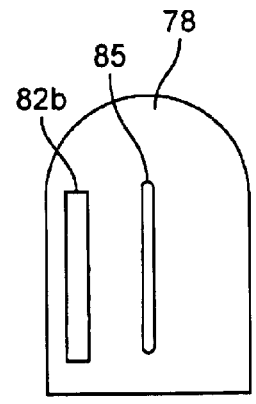
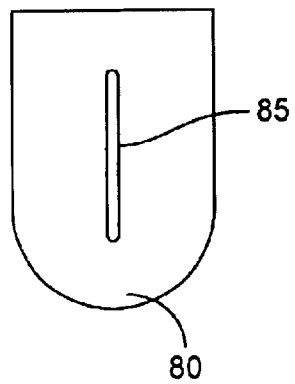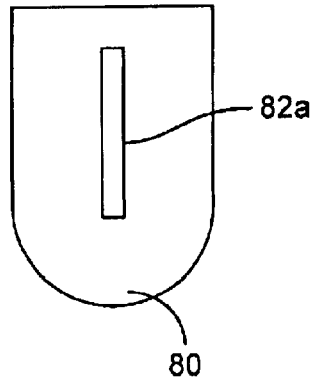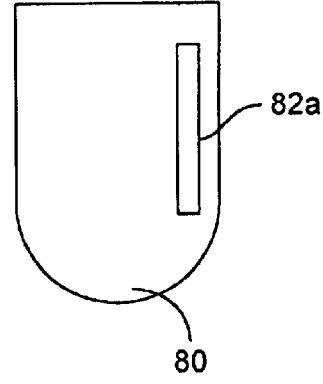
FIG. 8A    FIG. 8B    FIG. 8C

BIPOLAR CAUTERIZING INSTRUMENT

CROSS REFERENCES TO RELATED APPLICATIONS

The present application claims benefit, under 37 C.F.R. § 1.78, to U.S. Provisional Patent Application Ser. No. 60/258, 750, filed Dec. 9, 2000, entitled "Bipolar Cauterizing Instrument," the complete disclosure of which is incorporated herein by reference.

The present application is also related to U.S. patent application Ser. No. 09/418,726, filed Oct. 15, 1999 and U.S. patent application Ser. No. 09/415,568, filed Oct. 8, 1999, the complete disclosure of which are incorporated herein by reference for all purposes.

BACKGROUND OF THE INVENTION

The present invention relates generally to surgical tools and methods. More particularly, the present invention relates to a bipolar cauterizing and cutting tool for use with robotic surgical systems.

A significant number of different surgical instruments are used during each surgical procedure. In minimally invasive or robotic surgical procedures, the number of entry ports into a patient is generally limited because of space constraints, as well as the desire to avoid unnecessary incisions in the patient. Hence, a number of different surgical instruments will typically be introduced through the same trocar sleeve into the abdomen during, for example, laparoscopic procedures. As a result, the number of surgical instruments will often be attached and detached from a single instrument holder of a manipulator during an operation. Since each instrument change lengthens the surgical procedure and increases the patient's risk, it is beneficial to make a minimal amount of instrument changes during the surgical procedure.

Electrosurgery refers broadly to a class of medical procedures which rely on the application of high frequency electrical energy, usually radio frequency energy, to patient tissue to achieve a number of possible effects, such as cutting, coagulation, necrosis, and the like. Of particular interest to the present invention, bipolar electrosurgical procedures rely on contacting electrodes of different polarity in close proximity to each other against or into tissue. For example, in some minimally invasive and robotically controlled surgical procedures, tissue in the patient's body must be cauterized and severed. To perform such a procedure, bipolar or monopolar cauterizing grips can be introduced through the trocar to engage the target tissue. An electrical energy, such as radiofrequency energy, is delivered to the grips to cauterize the engaged tissue. Unfortunately, conventional cauterizing grips are insufficient to cut the cauterized tissue because they generally use the entire two grips as the two electrodes. The grips are designed primarily to grasp tissue and have a large surface area. The large surface area translates into a small power density and mkes them more effective as widespread heating (i.e. the size of the grips and some peripheral thermal damage to the surrounding tissue). Unfortunately, the heating does not concentrate the energy enough to allow for cutting of the gripped tissue. Thus, to achieve cutting of the cauterized tissue, a separate cutting instrument can be introduced into the body cavity through the trocar. However, the time associated with disconnecting the cauterizing grips from the body and connecting the cutting instrument to the robotic arm unnecessarily lengthens the surgical procedure and increases the risk to the patient.

One possible method of improving cauterizing and cutting with a robotic surgical system is to integrate a cutting element with the cauterizing grips. Unfortunately, because of the small size of the trocar and surgical instruments, it is difficult to integrate a cutting element with the cauterizing grips. Moreover, the incorporation of the cutting element in the grips is difficult because of the space available, especially with offset electrodes when trying to maintain a slim profile for good visualization.

In light of the above, it would be desirable to provide improved robotic surgery tools, systems, and method. It would further be desirable to provide a bipolar tool that can cauterize and cut tissue. It would be especially desirable if these enhanced robotic tools and techniques resulted in further improvement in the safety and reliability of the robotic surgical systems.

SUMMARY OF THE INVENTION

The present invention provides robotic systems, instruments, and methods for cauterizing tissue. In particular, the surgical instruments of the present invention are adapted to be used with a robotic system. The surgical instruments generally include opposing end effectors having grips that can engage the tissue. A current is delivered from an electrosurgical power source to electrodes disposed on the end effectors to cauterize the tissue. The electrode configurations provide efficient cauterization of the tissue. In particular, the positive and negative electrodes will be offset from each other so as to prevent shorting when the grips are closed and to provide a thin line of coagulation heating to the gripped tissue. Consequently, a small amount of tensioning force from the end effectors can sever the cauterized tissue without having to use a separate cutting element.

The surgical instruments will generally include an actuation mechanism that controls the orientation and movement of the distal end effectors. The actuation mechanism will typically be controlled by a robotic manipulator assembly that is controlled remotely by a user. For example, in one configuration, the actuation mechanism will be manipulated by the robotic manipulator assembly to move the end effectors between an open position and a closed position. In the closed position, the end effectors will contact the electrodes against the tissue to cauterize and/or sever the engaged tissue.

Some embodiments of the surgical instrument will include a wrist or rotatable body coupled to the distal end of the shaft to provide additional axes of rotation for the end effectors. For robotic surgery procedures, a plurality of degrees of rotation of the distal end effectors is preferred. For example, in many embodiments, the distal end of the surgical instrument will have two degrees of rotation, three degrees of rotation, or more.

The electrodes disposed on the end effectors are contacted against the tissue so that current will flow from one electrode to the other electrode through the engaged tissue. In some configurations the electrodes will both be disposed on the same end effectors. In other configurations, however, the positive electrode will be disposed on one end effector, and the negative electrode will be disposed on the other end effector. In either configuration, it is preferred that when the end effectors are in the closed position, the electrodes will be offset and spaced from each other such that delivery of a high frequency electrical energy will flow through the tissue between the electrodes without shorting the electrodes. Even if no tissue is between the end effectors, there will typically be a gap between the electrodes. When the end effectors are in the closed position the spacing between the negative and positive electrode will generally be between approximately 0.01 and 0.10 inches, and preferably between approximately 0.010 inches and 0.025 inches. It should be appreciated however, that the spacing of the electrodes will vary depending on the area, volume, width, material of the electrodes, and the like.

The electrodes of the present invention can be disposed directly in the end effectors or on nonconductive sleeves that are attached to the end effectors. The electrodes will generally be metal inserts or a conductive material deposited or etched onto the sleeves or end effectors. The electrodes will be electrically coupled to a conductive lead or to the grip drive shaft(s) so as to deliver the high frequency electrical energy to the engaged tissue. The electrodes and/or conductive wires will typically be composed of aluminum, copper, silver, tin, gold, tungsten, platinum, or the like.

As noted, the electrodes will usually be coupled to the end effectors with nonconductive sleeves or directly on the end effectors and insulated with bushings. The nonconductive sleeves can be removably placed over the end effectors to insulate the current carrying electrodes from the end effectors. If the electrodes are disposed directly on or in the end effectors, the insulating bushing can be positioned between the "live" electrode and the grip.

In alternative designs, the end effectors themselves (and the surrounding elements on the surgical instrument) can be composed of a nonconductive material. The nonconductive sleeves, end effectors, and bushing can be composed of a ceramic, a thermoset, a plastic such as Ultem®, a thermoplastic, or other high temperature nonconductive materials so that the only conductive portion of the distal portion of the surgical instrument are the electrodes.

In exemplary embodiments, one electrode will be disposed within a groove (either in the grip itself or on the nonconductive sleeve), while the other electrode can be disposed on a boss (either in the grip itself or on the nonconductive sleeve). When the end effectors are closed, the groove and boss interact in an interdigitating fashion. The interdigitating can apply tension to the tissue to help produce the cutting action. Applicants have found that by positioning the electrodes on a groove and boss that the tissue tends to wrap around the electrode so as to get better contact and better transfer of energy. Even in the boss and groove configuration, there will typically still be a gap between the positive and negative electrode.

The electrical energy can be delivered to the electrodes through the actuation drive shafts (e.g., cables) or through separate conductor wires. Accordingly, the drive shafts and conductor wires will usually be at least partially insulated so as to prevent current arcing to surrounding conductive elements in the instrument. If the drive shafts carry the electrical energy, they can be insulated in the main body of the device, but are typically not insulated through the wrist so that when the cables contact the end effectors, they transfer the energy to the end effectors. The end effectors can be separated by a non-conductive bushing to keep the two poles separate.

In one exemplary configuration, a sleeve or insulation layer can be disposed around at least a portion of the drive shaft(s) and the electrical energy can be delivered through the insulated drive shafts. In such a configuration, the distal portion of the surgical instrument (i.e., end effectors, pulleys, and wrist) can be at least partially composed of nonconductive material (such as a plastic or ceramic) so that the only "live" portion of the distal end of the instrument will be the end effectors, electrodes and cables.

In other arrangements, separate insulated conductor wires can be run through the shaft and wrist and attached directly to the electrodes disposed on the end effectors. In such an arrangement, the wrist, pulleys, and the like can be metal, since the conductor wires will only electrically contact the electrodes on the end effectors.

In one particular design, the conductor wires can be run outside of the wrist so as to allow for easy installation and replacement of the conductor wires. In such a design, the electrodes will typically be disposed on a removable and disposable sleeve.

In one particular aspect, the present invention provides a surgical instrument for use with a robotic arm. The surgical instrument includes a wrist rotatably coupled to a body. A pair of opposed end effectors are rotatably coupled to the wrist and are movable between an open position and a closed position. A first and second electrode are coupled to the end effectors. In the closed position, the first and second electrodes are spaced from each other so as to prevent shorting the electrodes.

In another exemplary embodiment, the present invention provides a bipolar tool for use with a robotic surgery system. The tool comprises first and second opposing end effectors rotatably coupled to a body. Nonconductive sleeves are disposed over the opposing end effectors and first and second electrodes are attached on the nonconductive sleeves. Conductors connect the first and second electrodes to an electrosurgical power source. An actuation mechanism moves the first and second end effectors between an open position and a closed position.

In another aspect, the present invention provides methods of cauterizing tissue. In an exemplary embodiment, the method includes providing a first grip and a second grip. A first electrode is in a groove on one of the end effectors and a second electrode is on a boss on the end effectors. The tissue is gripped between the first and second grip and a current is applied to the electrodes to cauterize the tissue.

Optionally, after the tissue has been cauterized, the tissue is tensioned between the end effectors to cut the tissue. Drive cables of the surgical instrument can be actuated with a robotic manipulator to close the end effectors about the tissue. In a particular embodiment, the electrical energy can be delivered to the electrodes through the drive cables.

In yet another method of cauterizing tissue, nonconductive sleeves are placed over a pair of end effectors. The tissue is gripped with the insulated end effectors and a current is delivered through electrodes disposed on the sleeves to cauterize the gripped tissue.

In another aspect, the present invention provides a robotic surgical system. The robotic surgical system will generally involve the use of a user interface and multiple robotic arms. One or more of the robotic arms will often support an articulated surgical tool, such as a bipolar cauterizer. The bipolar cauterizer can include a shaft and a pair of opposing end effectors. Electrodes will be coupled to the end effectors such that movement of the end effectors from an open position to a closed position will grip and cauterize tissue engaged by the electrodes. As the tissue is cauterized, the tension force created by the gripping of the tissue in conjunction with the electrode configuration can be sufficient to sever the gripped tissue.

In an exemplary configuration, a first electrode is disposed within a groove in the end effectors and a second electrode is disposed on a protruding boss on the end effectors. When the end effectors are moved to the closed position, the electrodes can interdigitate but will still be maintained in a spaced or offset configuration so as to prevent shorting. The spacing between the electrodes is typically between 0.010 inches and 0.10 inches. In one specific configuration, the electrodes will have a center to center distance of approximately 0.052 inches and a gap between the edges of approximately 0.022 inches. It should be appreciated however, that the spacing between the electrodes may change depending on the electrode configuration, current, the type of tissue being treated, or the like.

For a further understanding of the nature and advantages of the invention, reference should be made to the following description taken in conjunction with the accompanying drawings.

BRIEF DESCRIPTION OF THE DRAWINGS

FIG. 4A is a perspective view of an exemplary tool according to the principles of the present invention;

FIG. 4B illustrates a drive system of the present invention;

FIGS. 8A to 8C schematically illustrate various electrode configurations of the present invention;

DESCRIPTION OF THE SPECIFIC EMBODIMENTS

Robotic surgery will generally involve the use of multiple robotic arms. One or more of the robotic arms will often support a surgical tool which may be articulated (such as cauterizing grips, cauterizers, scissors, jaws, graspers, needle holders, microdissectors, staple appliers, tackers, suction/irrigation tools, clip appliers, or the like) or non-articulated (such as cutting blades, probes, irrigators, catheters, suction orifices, or the like). One or more of the robotic arms will often be used to support a surgical image capture device such as an endoscope (which may be any of the variety of structures such as a laparoscope, an arthroscope, a hysteroscope, or the like), or optionally, some other imaging modality (such as ultrasound, fluoroscopy, magnetic resonance imaging, or the like). Typically, the robotic arms will support at least two surgical tools corresponding to the two hands of a surgeon and one optical image capture device.

The robotic systems of the present invention will find application in a variety of surgical procedures. The most immediate applications will be to improve existing minimally invasive surgical procedures, such as coronary artery bypass grafting and mitral and aortic valve repair and/or replacement. The invention will also have applications for surgical procedures which are difficult to perform using existing minimally invasive techniques, such as Nissen Fundoplications. Additionally, it is anticipated that these surgical systems will find uses in entirely new surgeries that would be difficult and/or impossible to perform using traditionally open or known minimally invasive techniques. For example, by synchronizing the movements of the image capture device and/or surgical tools with a tissue undergoing physiological movement (such a beating heart), the moving tissue may be accurately manipulated and treated without halting the physiological movement. Additional potential applications include vascular surgery (such as for the repair of thoracic and abdominal aneurysms), general and digestive surgeries (such as cholecystectomy, inguinal hernia repair, colon resection, and the like), gynecology (for fertility procedures, hysterectomies, and the like), and a wide variety of alternative procedures.

While the remaining discussion generally relates to electrosurgical robotic surgery, it should be appreciated that the concepts of the present invention are also applicable to manually actuated electrosurgical surgical instruments or for other non-surgical robotically assisted methods and devices.

Figure 1:
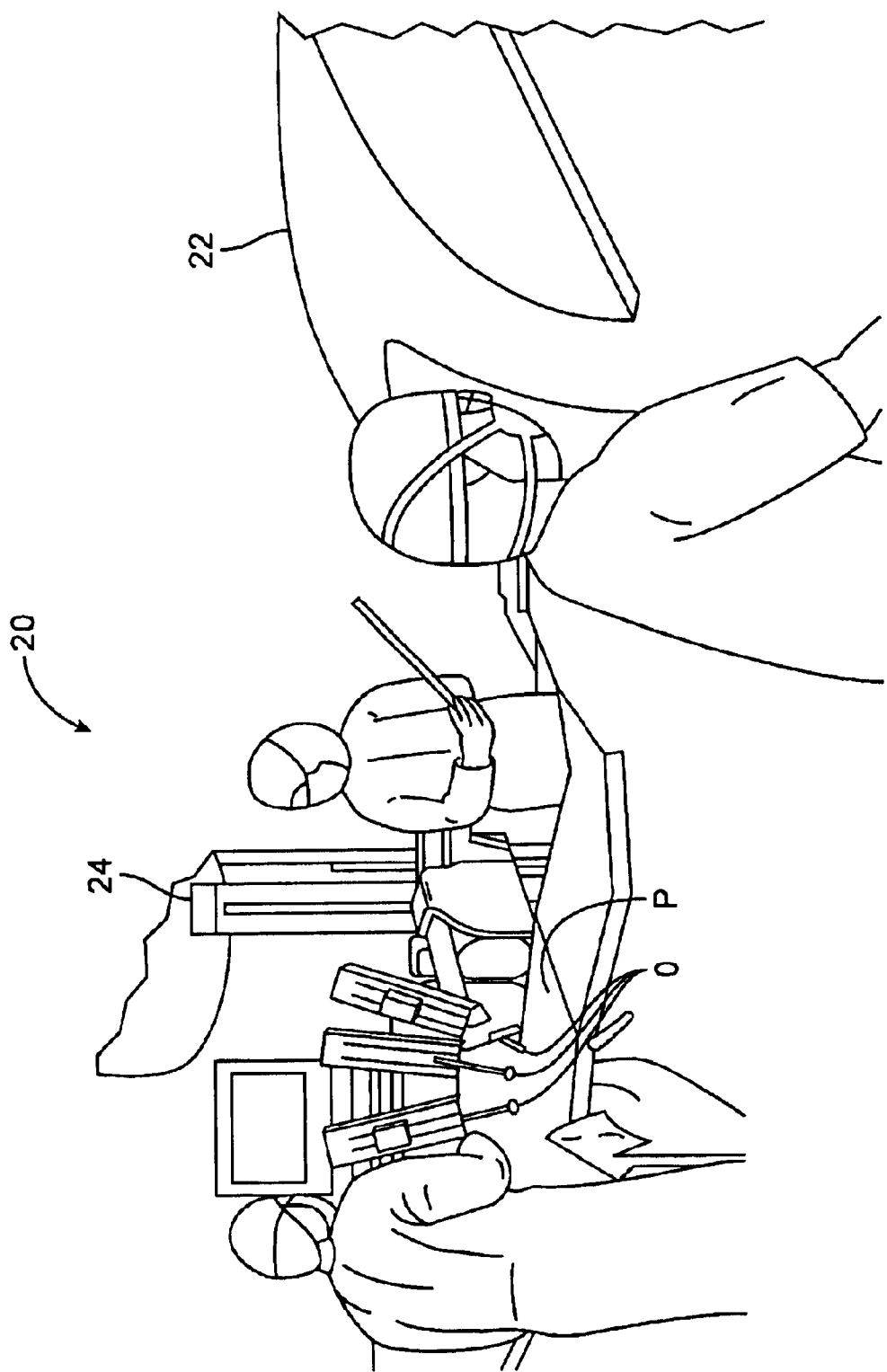
FIG. 1 illustrates a robotic surgical procedure in which a surgeon at a master station directs movement of robotic surgical tools effected by a slave manipulator, and shows an assistant preparing to change a tool mounted to a tool holder of the slave.

Referring now to FIG. 1, the robotic surgical system of the present invention 20 generally includes master controller 22 and a robotic arm slave cart 24. Master controller 22 generally includes master controllers (not shown) which are grasped by the surgeon and manipulated in space while the surgeon views the procedure view on a stereo display. The master controllers are manual input devices which preferably move with six degrees of freedom, and which often further have an actuatable handle for actuating tools (for example, for closing grasping jaws, applying an electrical potential to the electrode(s), or the like). In this embodiment, the master control station 22 includes a processor for processing the inputs from the surgeon.

Robotic arm cart 24 is positioned adjacent to patient body P and moves tools having shafts. The shafts extend into an internal surgical site within the patient body via openings O. As illustrated in FIG. 1, one or more assistant may be present during surgery to assist the surgeon, particularly during removal and replacement of tools. Robotic surgery systems and methods are further described in co-pending U.S. patent application Ser. No. 09/418,726, filed Oct. 15, 1999, and U.S. Pat. No. 6,132,368, the full disclosures of which are incorporated herein by reference.

Figure 2:
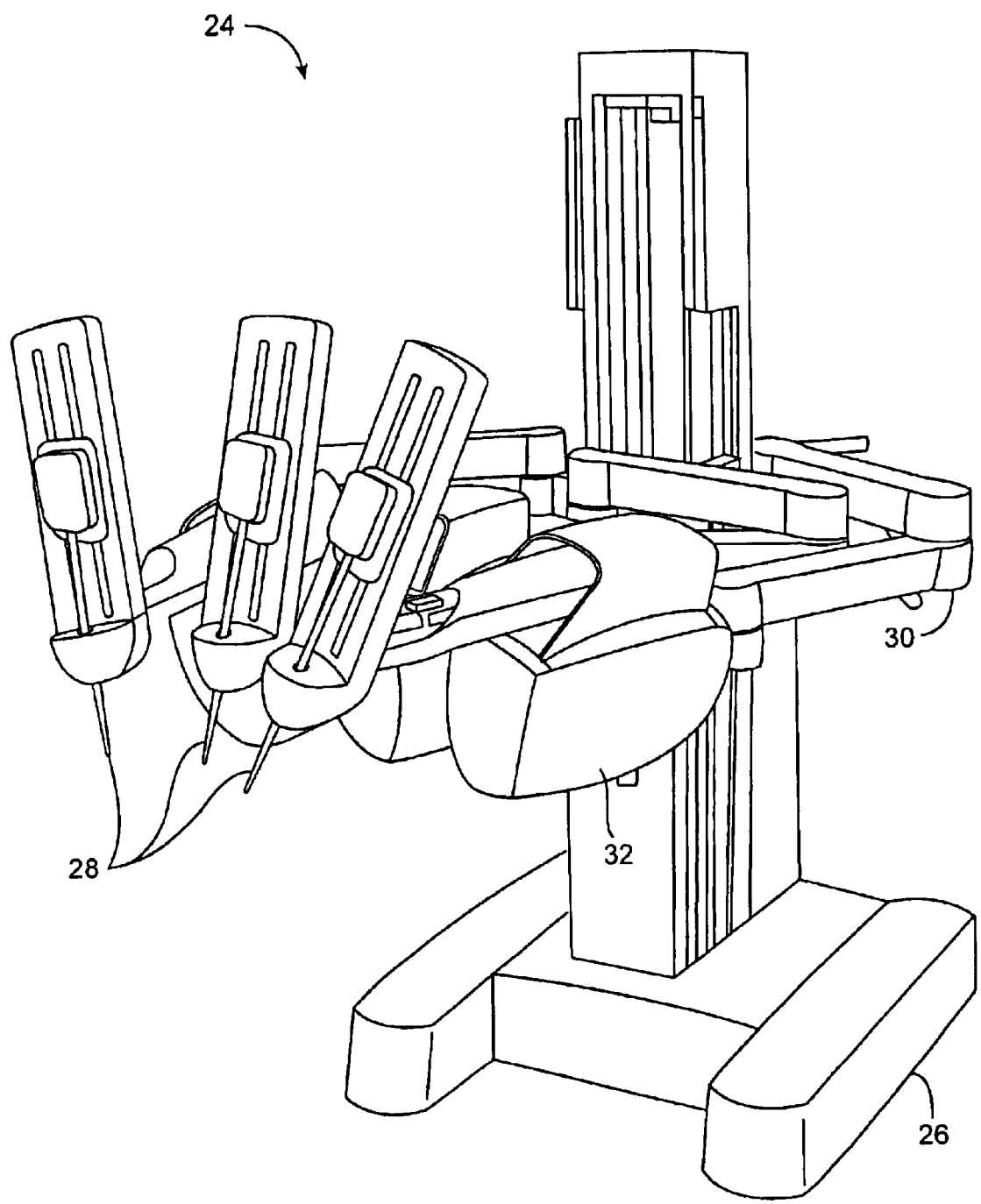
FIG. 2 is a perspective view of a robotic surgical arm cart system in which a series of passive set-up joints support robotically actuated manipulators (typically, the center arm would support a camera).

Robotic arm cart 24 is shown in isolation in FIG. 2. Cart 22 includes a base 26 from which three surgical tools 28 are supported. More specifically, tools 28 are each supported by a series of passive set-up joints 30 and a robotic manipulator 32. It should be noted that these structures are here illustrated with protective covers extending over much of the robotic linkage. It should be understood that these protective covers are optional, and may be limited in size or entirely eliminated in some embodiments to minimize the inertia that is manipulated by the servo mechanism, and to limit the overall weight of cart 22.

Cart 24 will generally have dimensions suitable for transporting the cart between operating rooms. The cart will typically fit through standard operating room doors and onto standard hospital elevators. The cart should have a weight and wheel (or other transportation) system that allows the cart to be positioned adjacent an operating table by a single attendant. The cart should have sufficient stability in the transport configuration to avoid tipping at minor discontinuities of the floor, and to easily withstand overturning moments that will be imposed at the ends of the robotic arms during use.

Figure 2A:
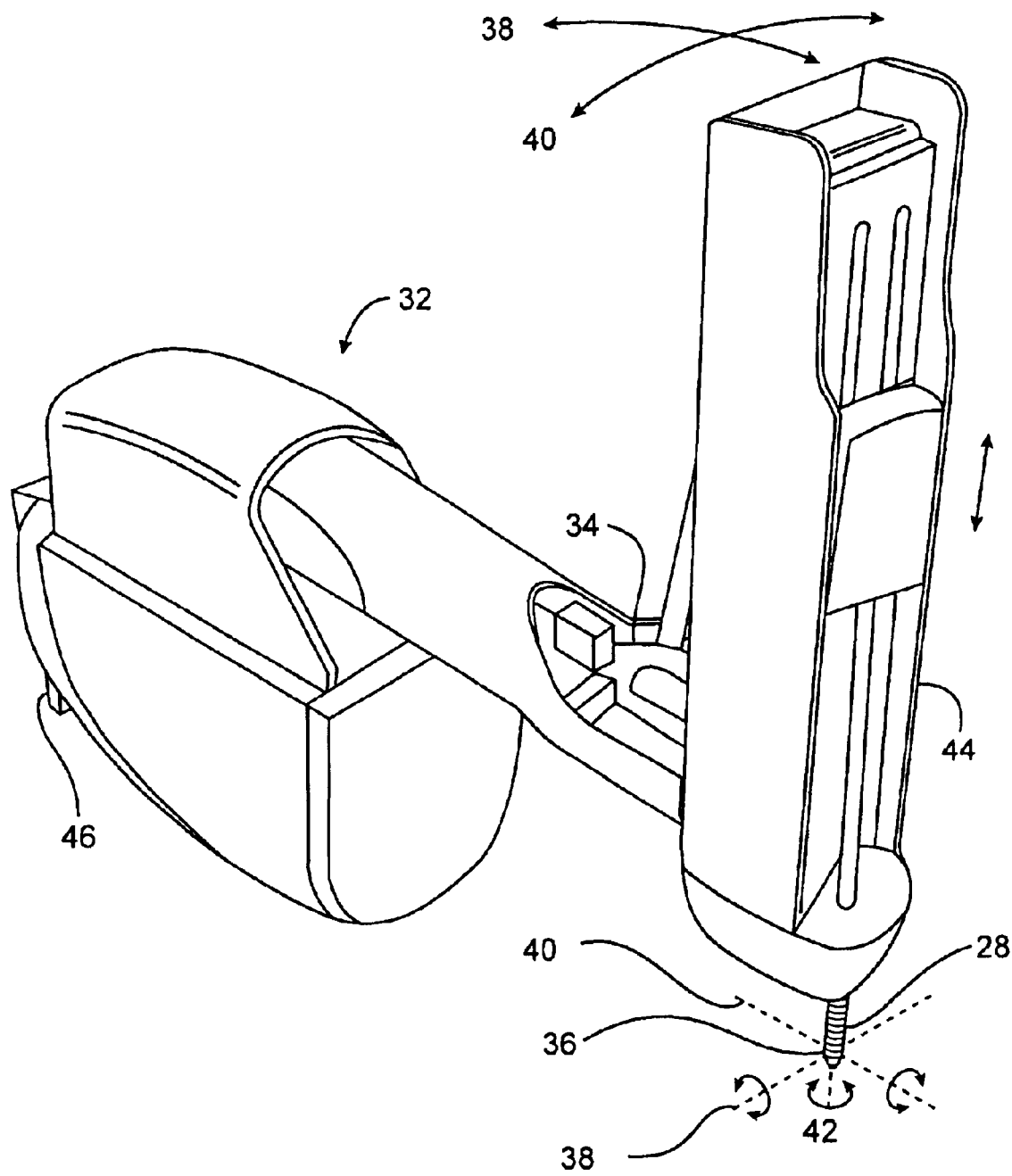
FIG. 2A is a perspective view of a robotic surgical manipulator for use in the cart system of FIG. 2.
Figure 2B:
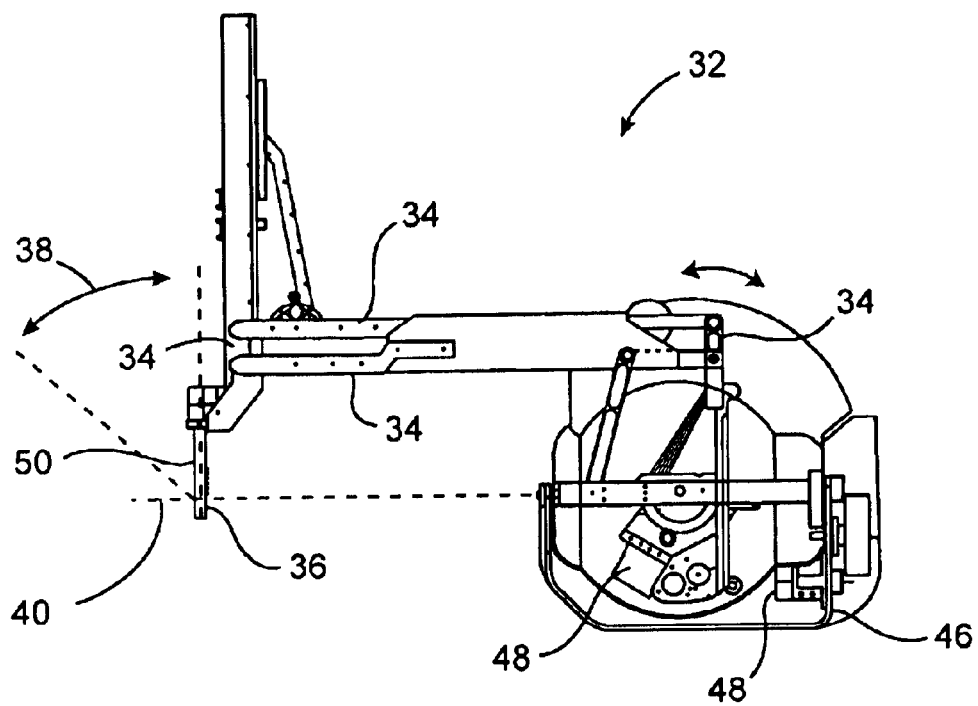
FIGS. 2B and C are side and front views, respectively, of the linkage of the robotic manipulator of FIG. 2, showing how the manipulator maintains a remote center of rotation along a shaft of the surgical tool.
Figure 2C:
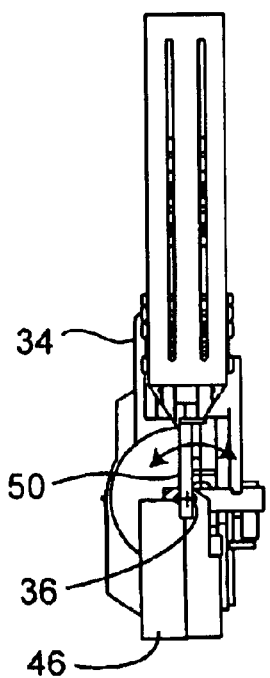

Referring now to FIGS. 2A–C, robotic manipulators 32 preferably include a linkage 34 that constrains movement of tool 28. More specifically, linkage 34 includes rigid links coupled together by rotational joints in a parallelogram arrangement so that tool 28 rotates around a point in space 36, as more fully described in issued U.S. Pat. No. 5,817,084, the full disclosure of which is incorporated herein by reference. The parallelogram arrangement constrains rotation to pivoting about an axis 38, sometimes called the pitch axis. The links supporting the parallelogram linkage are pivotally mounted to set-up joints so that tool 28 further rotates about an axis 40, sometimes called the yaw axis. The pitch and yaw axes intersect at the remote center 36, which is aligned along a shaft 44 of tool 28.

Tool 28 has driven degrees of freedom as supported by manipulator 32, including sliding motion of the tool along insertion axis 36 (the axis of shaft 44), sometimes referred to as insertion. As tool 28 slides along axis 42 relative to manipulator 32, remote center 36 remains fixed relative to base 46 of manipulator 32. Hence, the entire manipulator is generally moved to re-position remote center 36.

Linkage 34 of manipulator 32 is driven by a series of motors 48 (FIG. 2B). These motors actively move linkage 34 in response to commands from a processor. Motors 48 are further coupled to the tool so as to rotate the tool about shaft 44, and often to articulate a wrist at the distal end of the tool about at least one, and often two, and sometimes three or more degrees of rotation. Additionally, motors 48 can be used to actuate an articulatable end effector of the tool for grasping tissues in the jaws of a forceps or the like. Motors 48 may be coupled to at least some of the joints of tool 28 using cables and pulleys, as more fully described in U.S. Pat. No. 5,792,135, the full disclosure of which is also incorporated herein by reference. As described in that reference, the manipulator will often include flexible members for transferring motion from the drive components to the surgical tool. For endoscopic procedures, manipulator 32 will often include a cannula 50. Cannula 50 supports tool 28, allowing the tool to rotate and move axially through the central bore of the cannula.

Figure 3:
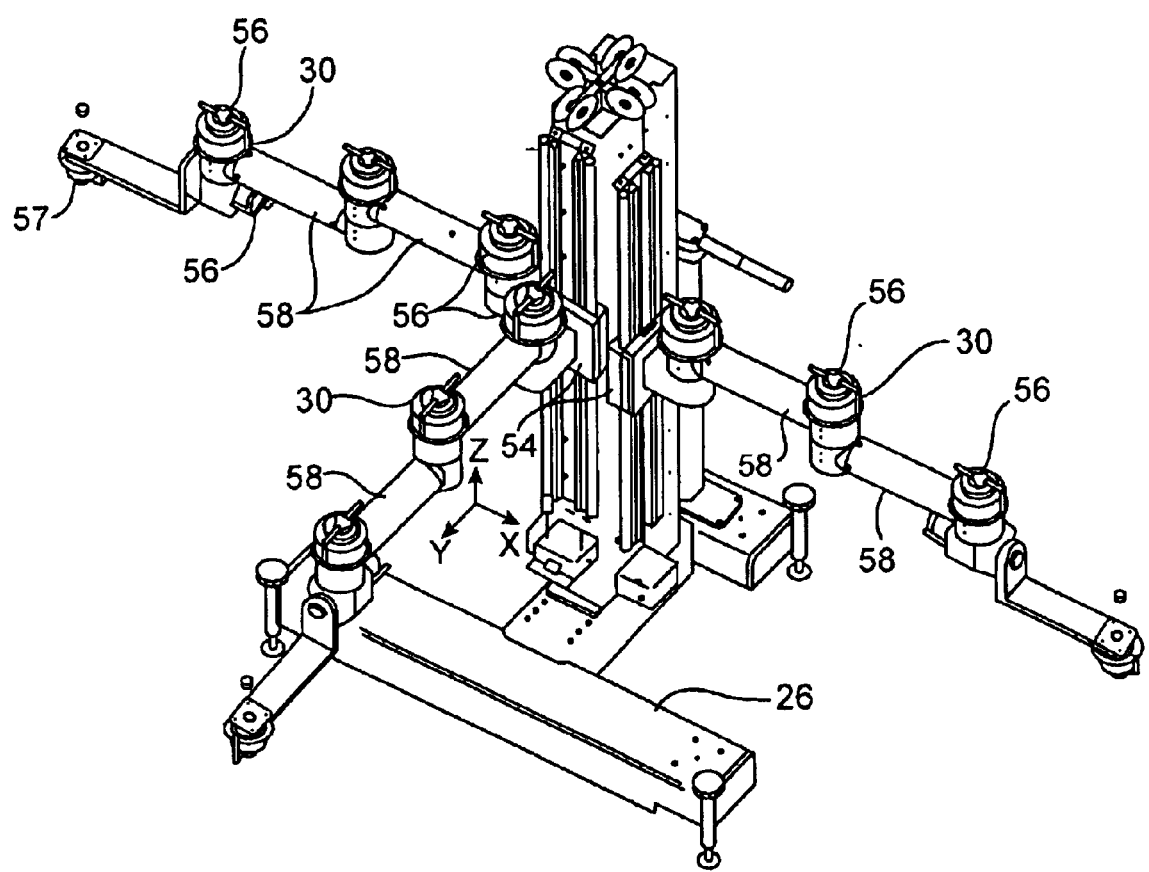
FIG. 3 is a perspective view of the cart structure and passive set-up joints which support the robotic manipulators in the system of FIG. 2.

As described above, manipulator 32 is generally supported by passive set-up joints 30. Exemplary set-up joint structures are illustrated in FIG. 3. The exemplary set-up joint system includes three types of structures. First, a vertical column 52 supports vertically sliding joints 54 that are used to position manipulator 32 along the vertical or Z axis. Second, rotary joints 56 separated by rigid links 58 are used to horizontally position manipulators 32 in the X-Y plane. Third, another series of rotary joints 57 mounted adjacent a manipulator interface 60 rotationally orients the manipulators.

The structure of column 52, vertical sliding joints 54, and base 26 can be understood with reference to FIG. 3. Beginning with base 26, the base will generally distribute the weight of the robotic structures and the forces imposed on the robotic arms. Column 52 extends upward from base 26, and may optionally comprise a box steel structure. Sliding joints 54 are counterbalanced by weights mounted with column 52. Sensors (typically in the form of potentiometers) indicate vertical position of sliding joints 54, and also indicate the rotational position of each rotary joint 56. As the structure of the joint elements is known, the processor can accurately determine the position and orientation of the manipulator base. As the position of the tool and tool end effector will be known relative to the manipulator base, the processor can further accurately determine end effector position and orientation, as well as how to effect movement in a desired direction by articulating one or more the driven joints.

Each of rotational joints 56 and slider joints 54 can include a brake. The brake prevents articulation about the joint unless the brake is released, the brake being normally on. The brakes at all the joints are actuated in unison by a button on the set-up joints, thereby allowing the operating room personnel to position the manipulator in space when the brake is released. Additional rotational joints similarly allow the orientation of the manipulator to be set while the brake is released. The exemplary set-up joint structure is more fully described in co-pending patent application Ser. No. 09/368,309, filed Aug. 3, 1999, the full disclosure of which is incorporated herein by reference.

Exemplary tools 28 of the present invention are illustrated in FIGS. 4A to 11. As shown in FIG. 4A, tool 28 generally includes a rigid shaft 62 having a proximal end 64 and distal end 66. A surgical end effector is coupled to shaft 62 through a clevis or wrist body 74 that can provide at least 1 degree of freedom, and ideally providing at least 2 degrees of freedom to the end effectors. A proximal housing 68 includes an interface 70 which mechanically and electrically couples the shaft and end effectors to the robotic manipulator.

As illustrated schematically in FIG. 4B, a drive system 76 mechanically couples first and second end effector elements 78, 80 to driven elements of interface 70. The actuating drive system 76 will typically include a plurality of drive shafts and pulleys to facilitate actuation of the end effectors. The drive system is more fully described in U.S. Pat. No. 5,792,135, the full disclosure of which is incorporated herein by reference. Stated simply, the drive system translates mechanical inputs from driven elements into articulation of the wrist 74 about first and second axes $A_1$, $A_2$, as well as into actuation of the end effectors 78, 80 by relative movement of the end effector elements about axis $A_2$ to move the end effectors between an open and closed position. In addition, as shown in FIG. 4A, the driven elements can effect rotation of the end effector about the axis of shaft 62 ($A_3$) by rotating the shaft relative to proximal housing 68, and allowing the cables to twist (within a limited angular range) within the shaft.

A wide variety of alternative drive systems might be employed, including alternative cabling arrangements, drive chains or belts, hydraulic drive systems, gear trains, or the like. In some of these drive systems, motion of end effectors about the axes may be coupled to multiple driven elements. In other embodiments, there may be a one to one correspondence between driven elements and motion of an end effector element about an axis. Still other embodiments may require fewer (or more) driven elements to effect the desired degrees of freedom, for example, when a single element end effector is provided. Hence, manipulation of the end effector via interface 70 will generally involve some reconfiguration of the robotic system during the tool change.

Figure 5A:
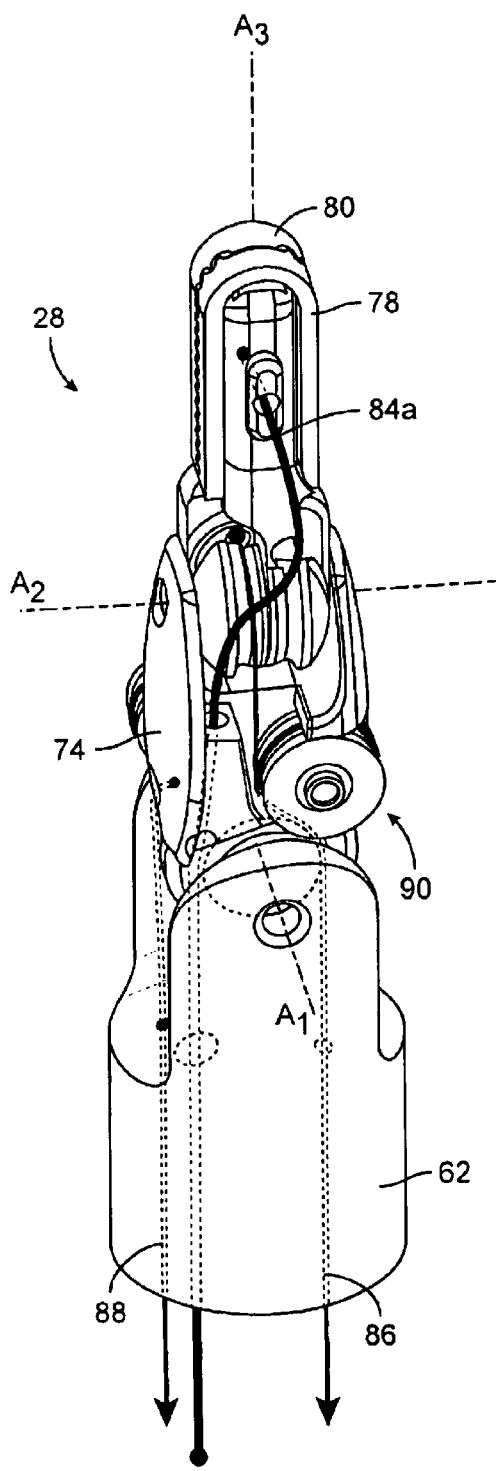
FIGS. 5A and 5B are close up views of a distal end of a surgical tool with the end effectors in a closed position.
Figure 5B:
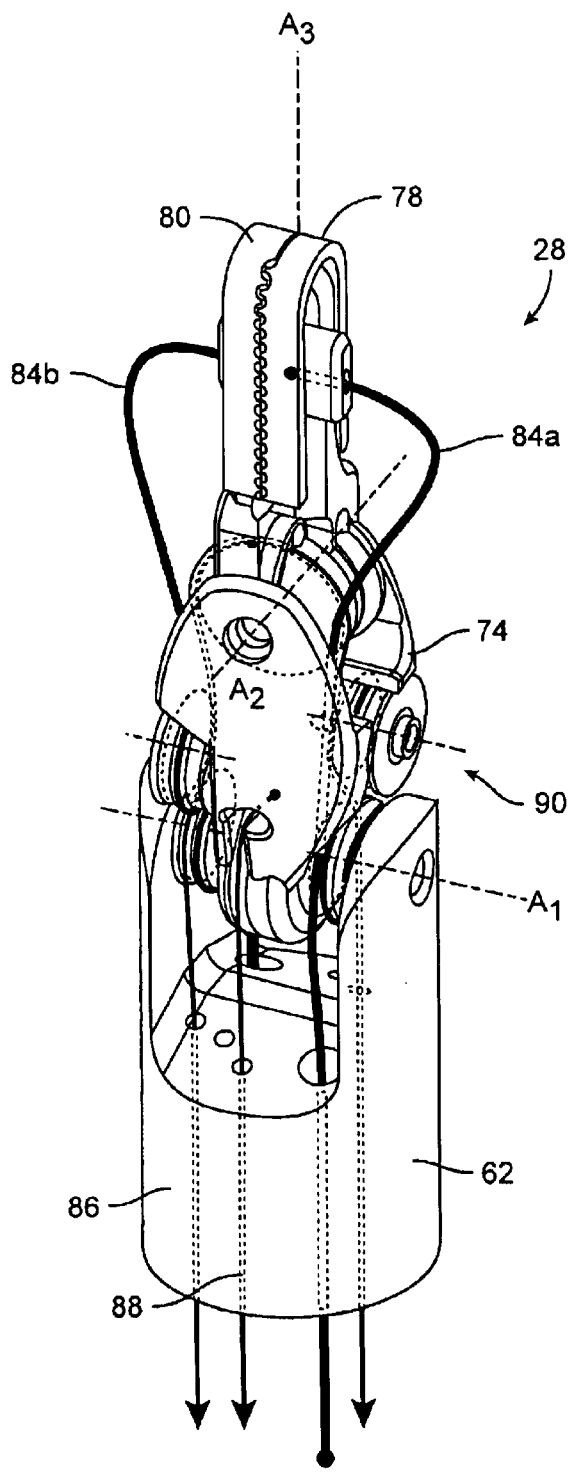

One exemplary bipolar cauterizer 28 that can be removably attached with the robotic surgical systems of the present invention is shown in FIGS. 5A and 5B. The cauterizer 28 includes a proximal clevis or shaft 62. A distal clevis or wrist body 74 is rotatably coupled to shaft 62 about the first axis $A_1$. End effectors 78, 80 are rotatably coupled to the wrist 74 about a second axis $A_2$. Both the end effectors and clevis can be rotatable about the longitudinal axis $A_3$ of the shaft 62. A negative and positive electrode 82a, 82b (shown most clearly in FIGS. 6A and 6B) can be coupled to the end effectors to deliver a high frequency electrical energy into tissue engaged by the jaws 78, 80.

The conductive electrodes 82a, 82b can be coupled to an electric power supply (not shown) through conductive leads 84a, 84b. In an exemplary embodiment, the conductive leads can be run from the proximal end of the instrument, through lumens in clevis 74 and up to the electrodes 82a, 82b disposed on the end effectors 78, 80. The distal portion of the conductive leads 84a, 84b can be run outside of the clevis 74 so as to allow for easy connection and disconnection of the conductive leads 84a, 84b from the electrodes.

Depending on the specific configuration of the cauterizer, the end effectors 78, 80 and drive system can be composed of a nonconductive material or a conductive material. In some embodiments, the electrodes can be insulated from the end effector with either a nonconductive bushing or sleeve that is composed of plastic, ceramic, Teflon®, Ultem®, or other non-conductive materials. If the electrodes are attached directly to the end effectors, an insulating bushing can be disposed between the conductive end effectors and the electrodes so that the only "live" portion of the surgical instrument are the electrodes.

The electrodes of the present invention are preferably made of a conductive material such as aluminum, stainless steel, platinum, tungsten, gold, or the like. The electrodes can be in the form of strips, deposited material, inserts, or the like. In some embodiments, the jaws themselves can be the electrodes.

For the bipolar methods of the present invention, the two electrodes on the end effectors should be at two electrical potentials and should not come in contact with each other. Thus, in most embodiments the electrodes are configured to have a gap between the electrodes even when the end effectors are in the closed configuration. As is the case with conventional electrosurgical instruments, a range of supply settings may be used for cutting, coagulation and the like. Moreover, it should be appreciated, that the electrodes can be configured in a wide variety of patterns and designs, some of which are illustrated in FIGS. 6 to 8C.

An exemplary power supply can create a wattage up to approximately 120 Watts of power for cauterizing the target tissue. Some exemplary radiofrequency power sources that can be used with the bipolar cauterizers of the present invention are manufactured by Valleylab, under the trade name Force FX. Alternatively commercially available units such as Valleylab Force EZ, Erbe Erboton ICC 350 and the like, may be used. The voltage used with bipolar cauterizer 28 is generally between 0 V and 1000 V peak-to peak, and preferably between 100 V and 500 V. As long as the jaws and electrodes are both in good contact with the tissue intended to be cauterized and cut, there is much less chance of voltage from the electrodes arcing to other conductive components on the instrument (e.g., the wrist, shaft, or pulleys). It should be appreciated, however, that the voltage setting of the electrosurgical power generator will vary depending on the specific dimensions of the electrodes, the tissue to be treated, and the like.

In exemplary embodiments, movement of end effectors 78, 80 are effected through mechanical actuation of a yaw cable 86 and pitch cable 88 via surgeon input devices. Actuation of the pitch cable 88 can rotate the end effectors 78, 80 about the wrist axis $A_1$, while actuation of the yaw cable 86 moves the jaws about axis $A_2$, an axis that is substantially perpendicular to axis $A_1$, between an open and closed position. Typically, the cables 86, 88 are directed through lumens in the shaft and wrist body and through a conductive or nonconductive pulley assembly 90.

As shown in FIGS. 6A to 7B, in one configuration the end effectors 78, 80 include a jaw body 92 and a pivot body 94. Nonconductive sleeves 96 can be removably coupled to jaw body 92 to attach electrodes 82a, 82b to the end effector. As shown, the sleeves 96 include grip surfaces 98 that can contact and grip the target tissue. The electrodes 82a, 82b can be molded inserts or a conductive material etched or deposited onto the sleeves. The nonconductive sleeves can include a slot 100 for receiving the jaw body 92 so as to insulate the end effectors from the conductive electrodes. In some configurations, the electrodes and grip surfaces of the jaws can be "non-stick," such as coated with a non-stick polymer, e.g., Teflon®. The conductive leads can be routed through openings 102 in the sleeves 96 and jaw body 92 to contact the electrodes 82a, 82b.

The sleeves 96 are preferably disposable so as to allow the physician to replace the sleeves between each surgical procedure, if desired. The conductive leads 84a, 84b can also be detachable from the electrodes 82a, 82b so as to decouple the electrodes from the power supply. During or after the surgical procedure, the sleeves 96 and the electrodes 82a, 82b can be removed from the jaw body 92 and replaced. Thus, different sized electrodes, a different tooth configuration on the end effectors, a different configuration of electrodes, or the like, can be easily attached to the jaw body 92. In such arrangements, to allow for easy detachment, the conductive leads 84a, 84b can be routed through a lumen in the wrist and to an unprotected path outside the wrist. In other embodiments, the jaws 78, 80, wrist 74, and pulleys 90 can be composed of a nonconductive material and the electrodes can be directly coupled to the end effectors. Consequently, non-conductive bushings can be positioned between the end effectors, and nonconductive sleeves that overly the jaw body 92 are not needed.

Figure 6A:
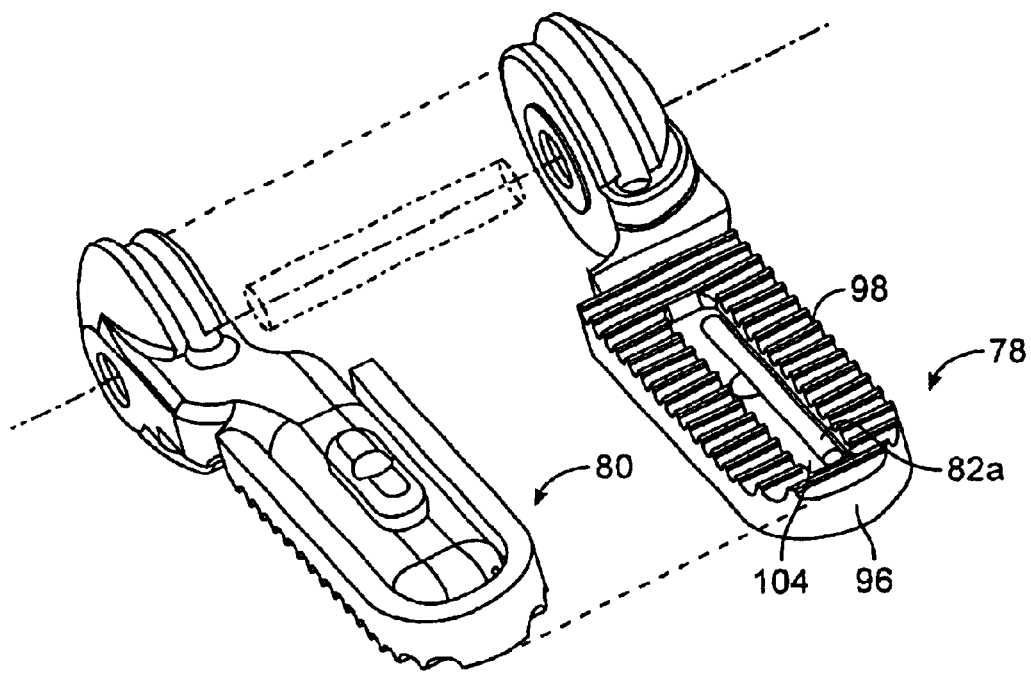
FIG. 6A illustrates a first grip with a recessed electrode.
Figure 6B:
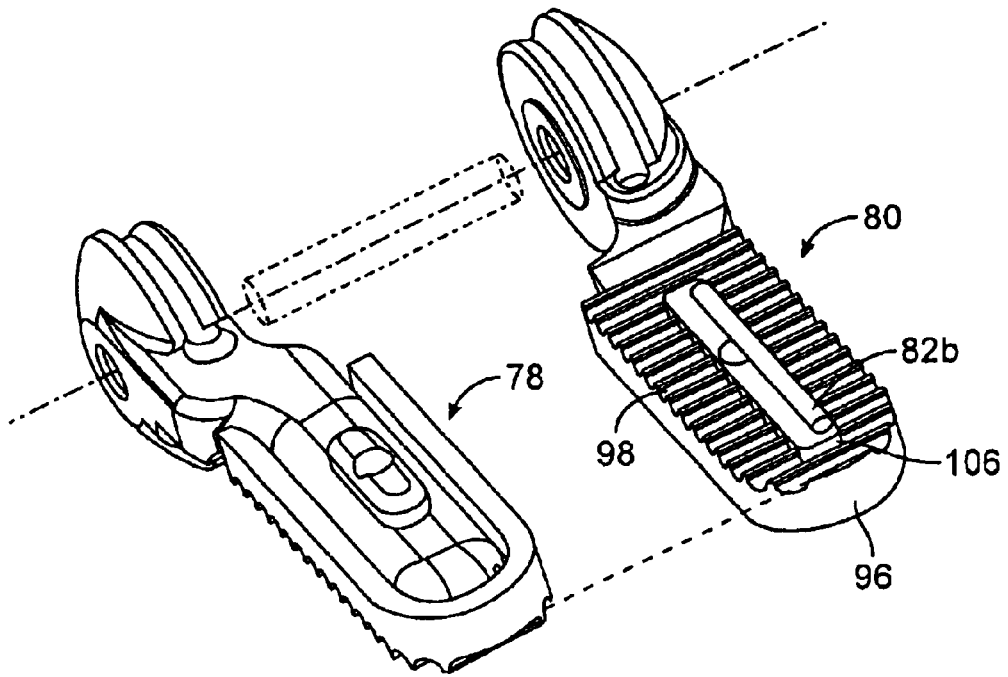
FIG. 6B illustrates an opposing second grip with a raised electrode.
Figure 7A:
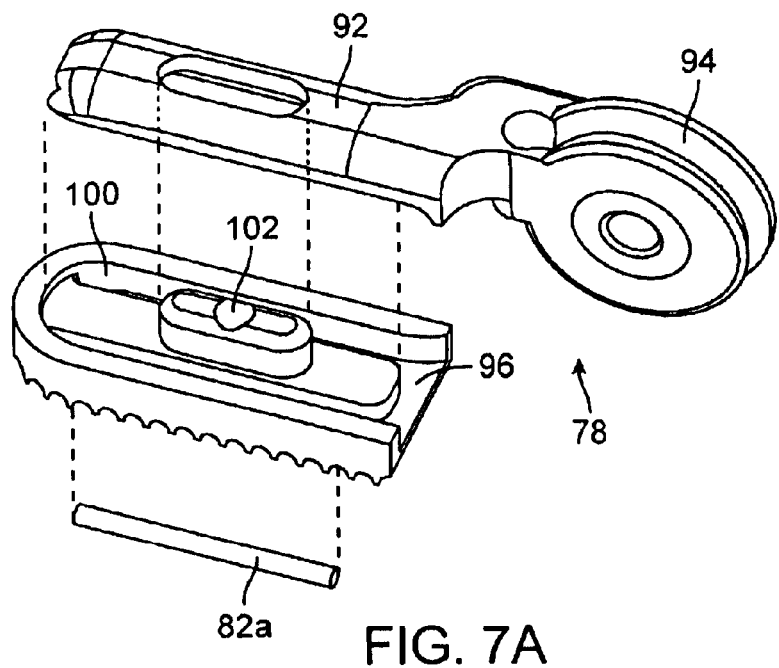
FIGS. 7A and 7B are exploded view showing the electrode, sleeve, and jaw blade.
Figure 7B:
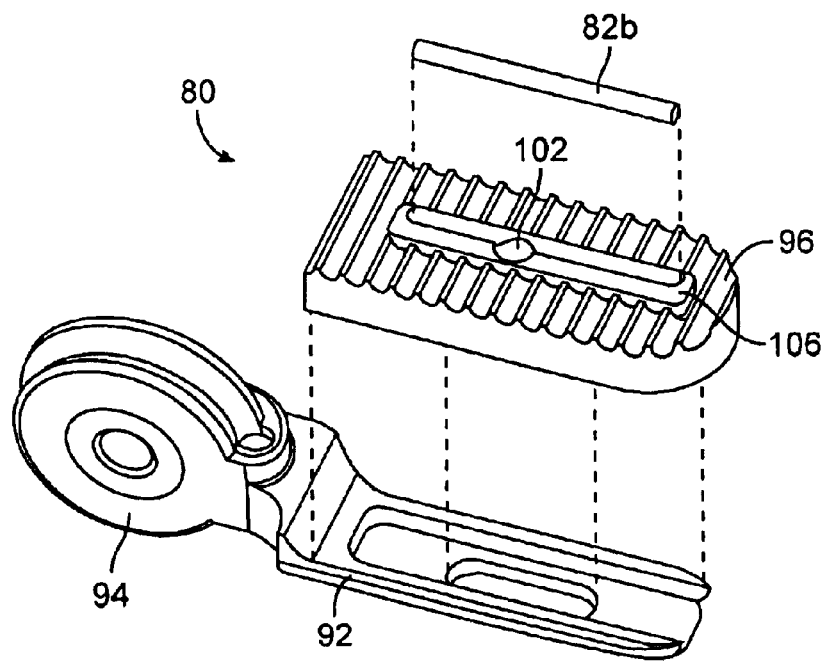

In exemplary arrangements, as shown most clearly in FIGS. 6A and 6B, the first electrode 82a will be disposed in a groove 104 on the jaw or sleeve and the second electrode 82b will be disposed on a boss 106. When the end effectors are moved to the closed position, the boss 106 and groove 104 will interdigitate while still maintaining a gap between the two electrodes. The boss and groove configuration has been found to create thin coagulation heating lines in the tissue when current is delivered between the electrodes. The thin heating lines in the tissue make it easy for the user to cut and separate the tissue by applying a small amount of tension. The time of heating will depend primarily on the size of the tissue being coagulated, the electrode configuration, the current, and the like.

It should be appreciated that the electrodes can be positioned on opposing end effector or on the same end effector. Moreover, the electrodes do not have to be disposed within a groove or on a boss. The electrodes can contact the engaged tissue disposed between the electrodes 82a, 82b and a current is applied between the spaced electrodes to deliver a current flow to cauterize the tissue. If desired, a tension force applied from the end effectors can cut the tissue along the cauterization heat lines to separate the tissue. As shown in phantom in FIGS. 8A to 8C, the jaws can optionally include a cutting blade 85 disposed on the jaws to facilitate cutting of the tissue. The blade 85 can be stationary or spring loaded and may be conductive or nonconductive.

In the exemplary electrode embodiments illustrated schematically in FIGS. 8A–8C, the electrodes will be placed in an offset and spaced configuration such that when the jaws are moved to the closed position there will be a gap between the electrodes so as to prevent shorting. As shown in FIG. 8A, in some embodiments a first electrode 82a will be positioned on first jaw 78 and second electrode 82b will be positioned on second jaw 80 (FIG. 8A). When the jaws are moved to the closed position, the electrodes will be positioned in a parallel arrangement with a gap between the electrodes.

In an alternative embodiment shown in FIG. 8B, both of the electrodes 82a, 82b can be disposed on the first jaw 78. Thus, when the first jaw 78 and second jaw 80 are moved to the closed position, the engaged tissue will be contacted with both the first and second electrode without shorting.

In yet another embodiment shown in FIG. 8C, the first jaw 78 can have a first electrode 82a disposed substantially in the center. The second jaw 80 can have a second electrode 82b and third electrode 82c disposed adjacent the edge of the grip such that when the jaws are moved to the closed position, the second electrode 82b and third electrode 82c will be disposed on both sides of the first electrode 82a.

While not shown, both of the electrodes 82a, 82b can be disposed in grooves on opposite jaws 78, 80 such that when the jaws are in the closed configuration, there is still space between the electrodes 82a, 82b.

Figure 9:
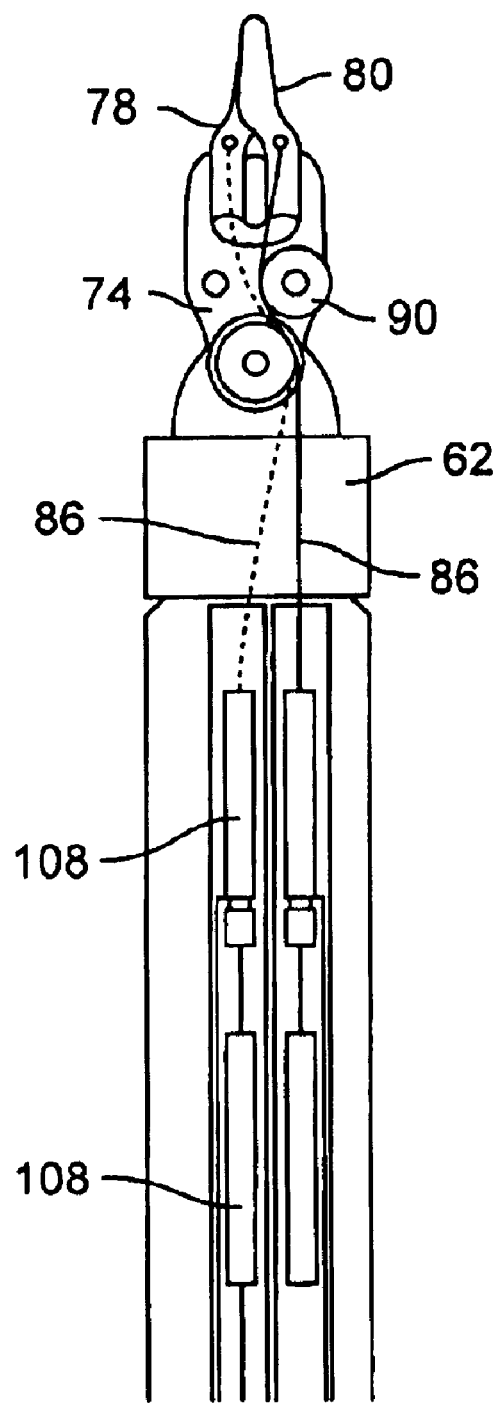
FIG. 9 illustrates an embodiment of the bipolar cauterizer in which a current is delivered through drive cables.
Figure 10A:
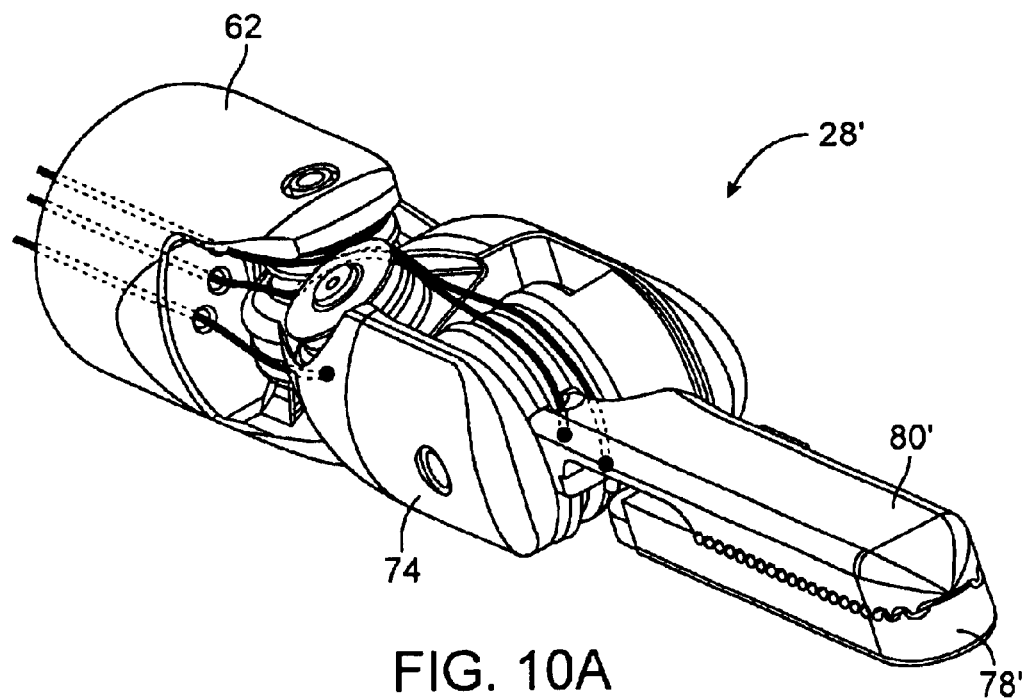
FIG. 10A shows another embodiment of a bipolar cauterizing end effectors with the end effectors in a closed position.
Figure 10B:
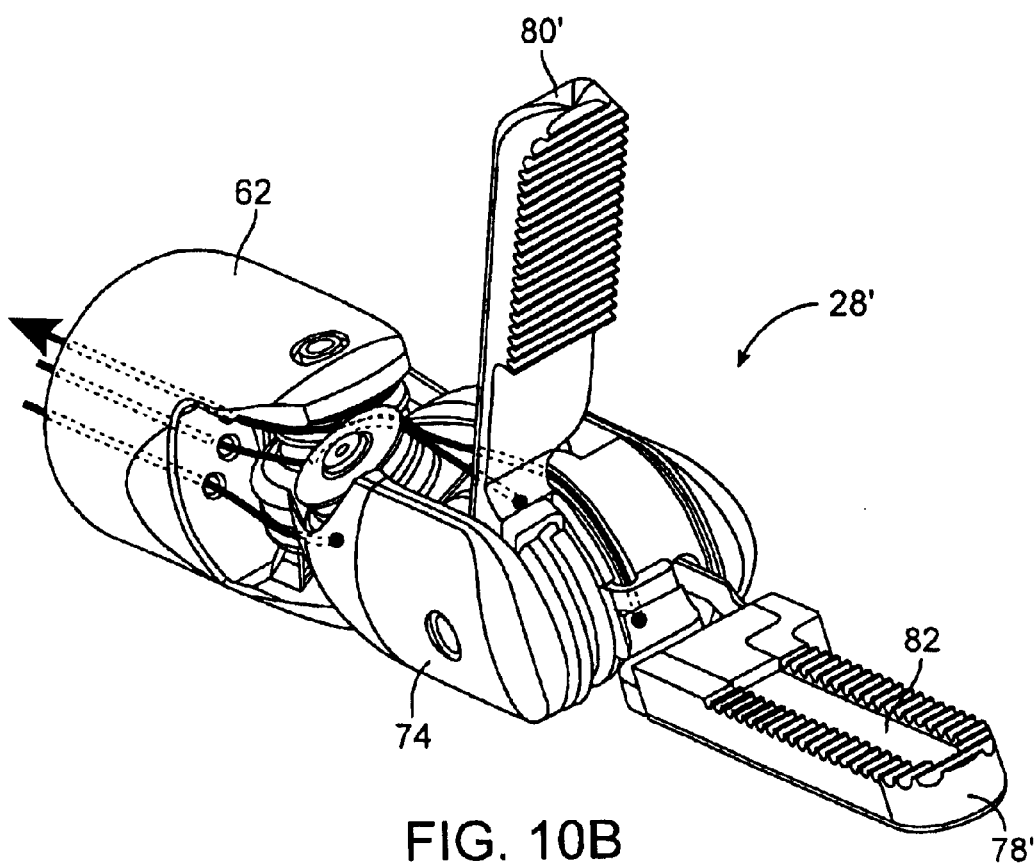
FIG. 10B shows the embodiment of FIG. 10A with the cauterizing end effectors in an open position.
Figure 11A:
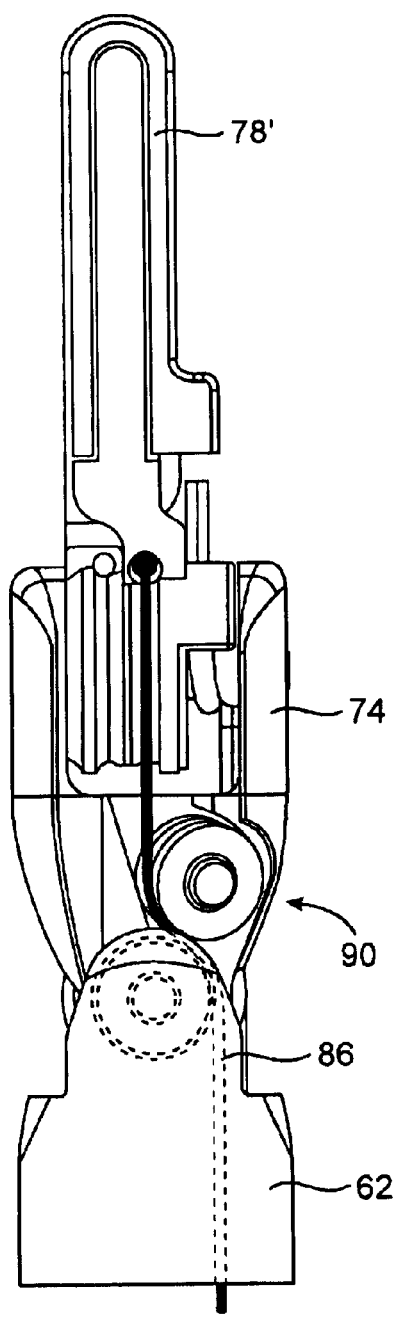
FIGS. 11A and 11B show left and right elevational views of the cauterizing end effectors of FIG. 10A.
Figure 11B:
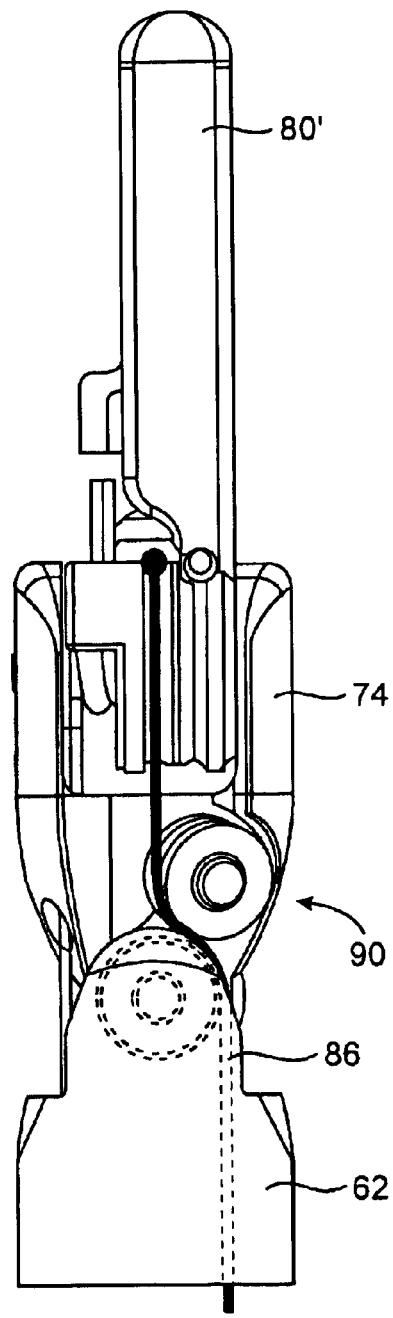

FIG. 9 schematically shows an embodiment of the bipolar cautery instrument 28 that uses at least one of drive shafts 86, 88 to deliver the voltage to cauterize the tissue at the target site. In such embodiments, each of the jaws 78, 80 and drive cables 86, 88 should be electrically isolated from each other. Since the yaw cables 86 run through shaft 62 of the instrument and can contact the pitch cables 88 as well as other drive shafts, the drive shafts carrying the current need to be insulated. Consequently, hypotubes 108 or other insulating members which the cables can coupled around or attached to at least a proximal portion of the drive shafts. This can prevent the current from traveling from the end effectors to the other conductive portions of the instrument. The distal portion of the drive cables also need to be insulated from each other at the distal end of the instrument. For example, to insulate the distal wrist 74 from the end effectors a combination of the following could be done: (1) make the shaft and wrist of a nonconductive material (e.g., plastic or ceramic), (2) put a nonconductive material bushing over a distal pin that the end effectors rotate about, (3) modify the end effectors so metal of one grip does not contact the metal of the other grip, and (4) make distal and proximal pulleys of a nonconductive material.

FIGS. 10A to 14 illustrate an alternative embodiment of the cauterizing instrument 28' of the present invention. As shown in FIGS. 10A, 10B, 11A, and 11B, similar to the above embodiments, the cauterizer 28' includes a proximal clevis or shaft 62. A distal clevis or wrist body 74 is rotatably coupled to the shaft 62 about the first axis $A_1$. End effectors 78, 80 are rotatably coupled to the wrist 74 about a second axis $A_2$. Both the end effectors and clevis can be rotatable about the longitudinal axis $A_3$ of the shaft 62. Yaw and pitch cables 86, 88 are attached to the end effectors and disposed through a pulley assembly 90 to actuate movement of the end effectors between an open and closed configuration about axis $A_1$ and to rotate the end effectors about wrist axis $A_2$. Movement of the end effectors is effected through actuation of a pitch and yaw cable, as described above. The end effectors 78', 80' of this embodiment include a first, solid conductive jaw 80' that can be ground through the shaft of the cauterizer and a second jaw having an electrode 82.

Figure 12A:
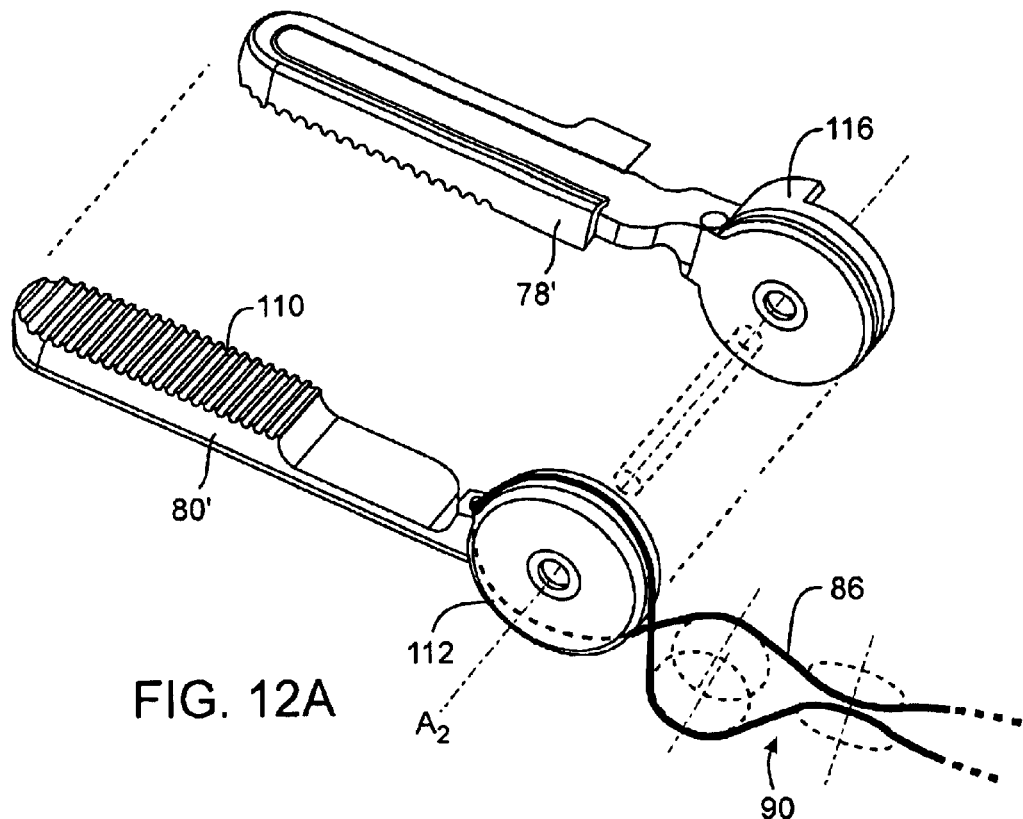
FIGS. 12A and 12B are partially exploded views showing elements of the end effector.

Referring now to FIG. 12A, the first end effector 80' will have a grip 110 attached to a pivot body 112. Yaw cable 86 will extend through the pulley assembly 90 and around pivot body 112 such that movement of yaw cable 86 causes rotation of the first end effector 80' about the pivot axis $A_2$. In the illustrated embodiment, the first end effector does not have a connection to a power supply and the treatment of the gripped tissue can be through a monopolar energy. The conductor 84 may be connected to a conventional electrosurgical power supply configured for monopolar energy to supply electrical energy to electrode 82. The circuit may be complete by grounding grip 110, to be functionally a second electrode, by a conductive path through the instrument clevis and shaft, or by an optional second conductive lead. Although monopolar energy is thus employed, the embodiment is "bipolar" in that current flow is confined to the gap between the grips. However, if bipolar energy delivery is desired, in other embodiments, the first end effector can have the same structure as the second end effector, as described below.

Figure 12B:
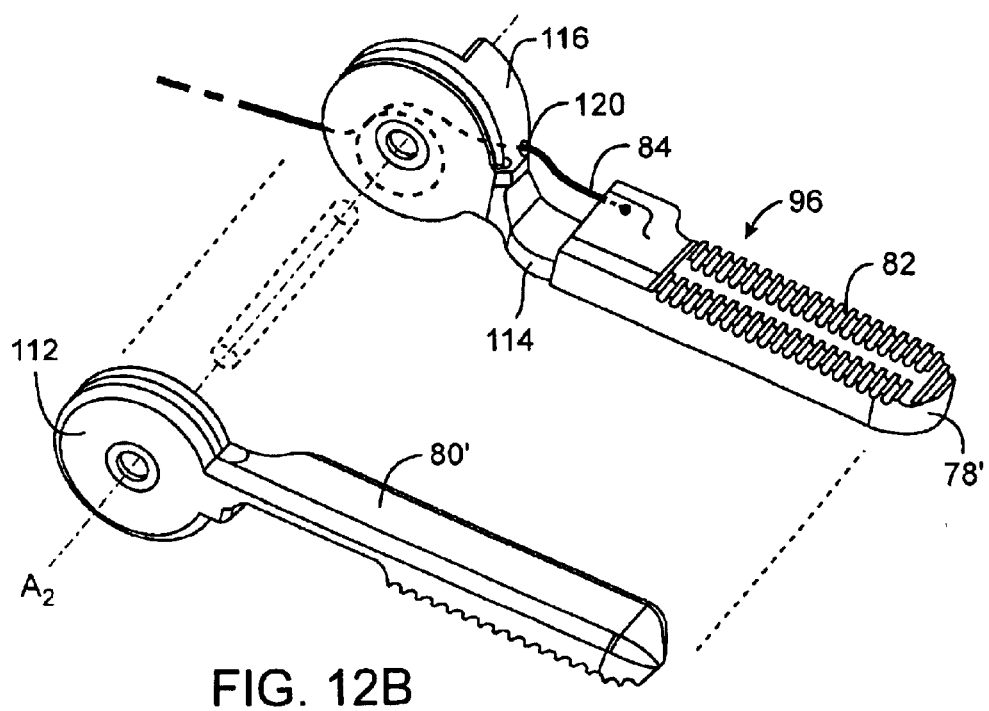
Figure 13:
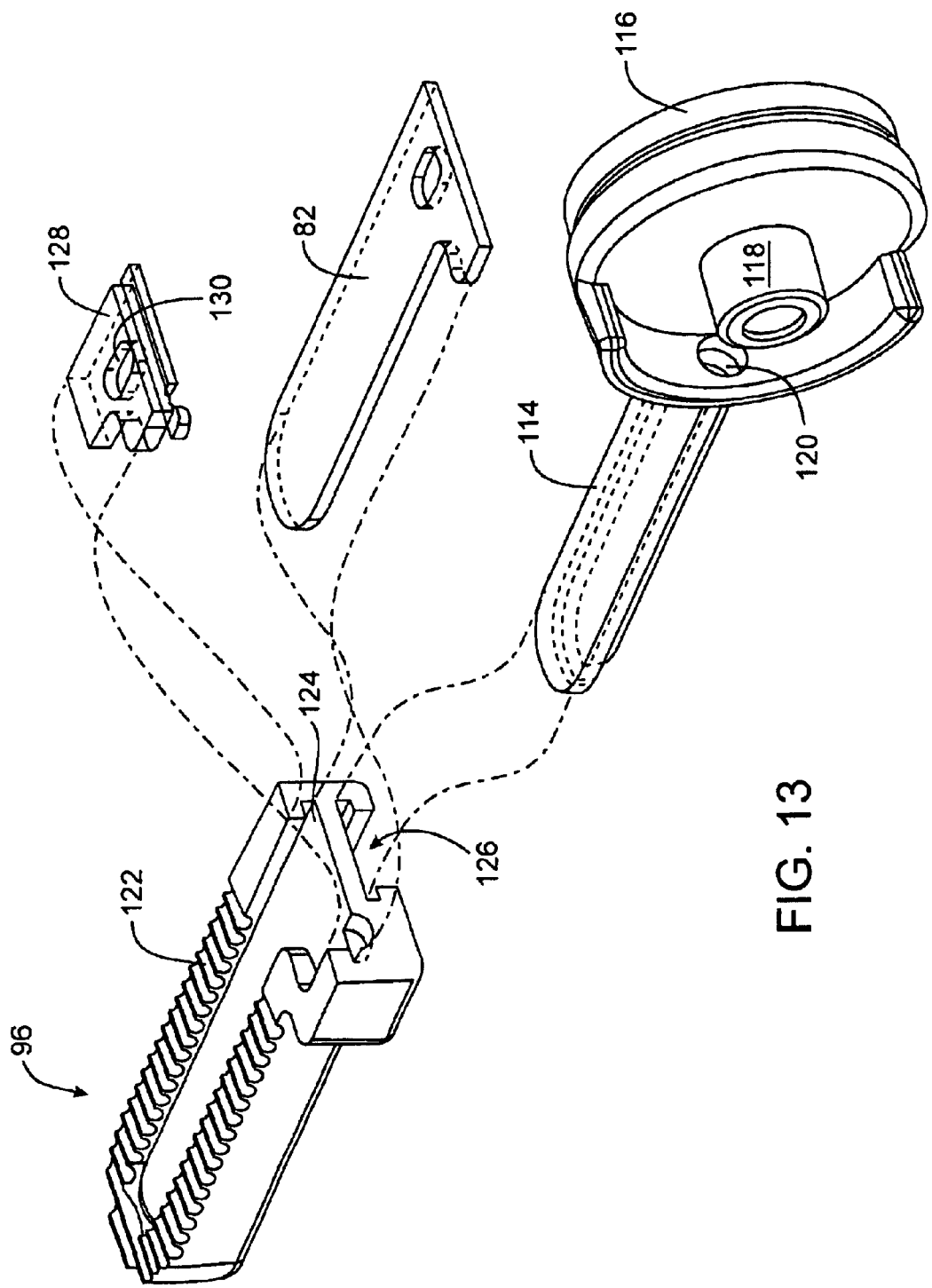
FIG. 13 is an exploded view illustrating the interaction of an exemplary sleeve, electrode and jaw blade.

FIGS. 12B and 13 most clearly illustrate the second end effector 78'. The second end effector 78' comprises a body comprising a jaw blade 114 and a pivot body 116. The pivot body 116 allows for rotation of the jaw body 114 about axis $A_2$. As shown in FIG. 12B, the pivot body 116 typically includes a conductor loop 118 and an opening 120 that can receive the conductive lead 84.

Note that alternatively, each of the opposed pair of end effector may comprise a sleeve-electrode-jaw-pulley assembly of the kind shown in FIG. 13, the opposed electrodes 82 being adjacent one another when the end effector is in the closed position. A second conductive lead 84 may be provided to couple the second electrode 82 to a power supply. The sleeve-electrode assembly 96, 82 may be removably, replaceably mounted, and may be disposable. Optionally, each electrode may be coupled to a bipolar power supply.

Removable insulating sleeve 96 will be used to couple the electrode to the jaw body 114. In the embodiment shown, the insulating sleeve has grips 122 for contacting the target tissue, a slot 124 for receiving the electrode 82, and a slot 126 for receiving the jaw blade 114. Electrode 82 can be delivered into electrode slot 124 in the sleeve and locked into place with a retainer clip 128. The retainer clip 128 can have an aperture 130 such that conductive lead 84 can extend through opening 120 in the pivot body, through aperture 130 in the retainer clip and into contact with the electrode. If desired, electrode 82 can also include an opening to facilitate better contact with conductive lead 84. While not shown, a yaw cable can be positioned around pivot body 116 to actuate rotation of the second end effector about axis $A_2$.

If desired, the jaws 132 may optionally be replaceably, removably mounted to the pulley assembly 136, 138 so as to electrically couple to conductive lead 84 when mounted to the pulley. The jaw mounting may include a snap-fit mounting, spring-clip mounting or secure frictional mounting, for example as described in the above mentioned U.S. Pat. application Ser. No. 09/415,568, filed Oct. 8, 1999, entitled "Minimally Invasive Surgical Hook Apparatus And Method For Using Same", the full disclosure of which is incorporated by this reference.

Figure 14:
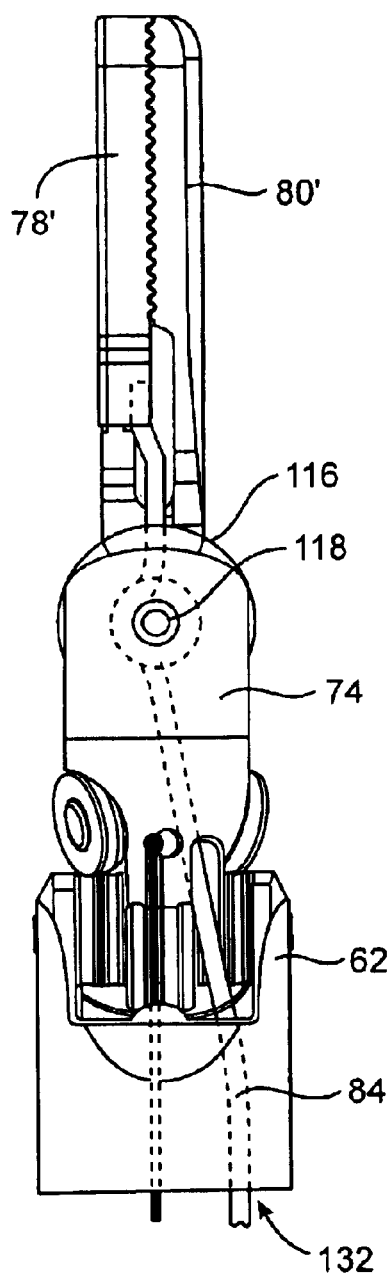
FIG. 14 illustrates a path of the conductive lead through the shaft and clevis.
Figure 15:
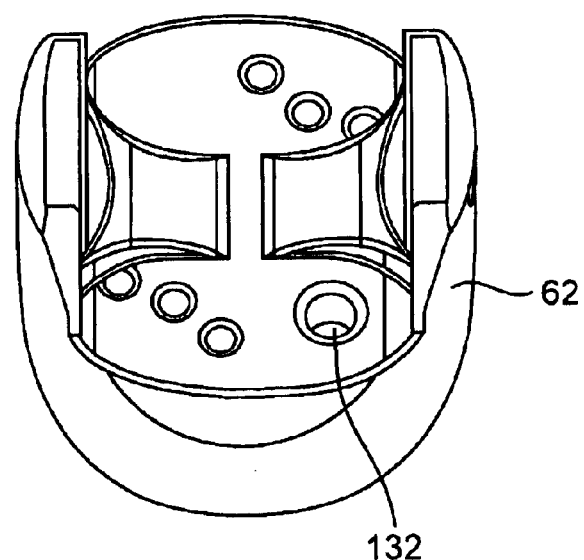
FIG. 15 is a top view of a shaft body having a plurality of lumens.

As shown in FIGS. 14 and 15, conductive lead 84 can extend through a lumen 132 in shaft 62 and wrap around conductor loop 118 in the pivot body 116 of the second end effector 78' and extend through the opening 120 to contact the electrode 82 that is disposed on jaw body 78'. As shown further in FIG. 15, shaft 62 typically includes a plurality of lumens that extend through at least a portion of the shaft for receiving the yaw cable 86, pitch cable 88, and one or more conductive leads 84.

Figure 16B:
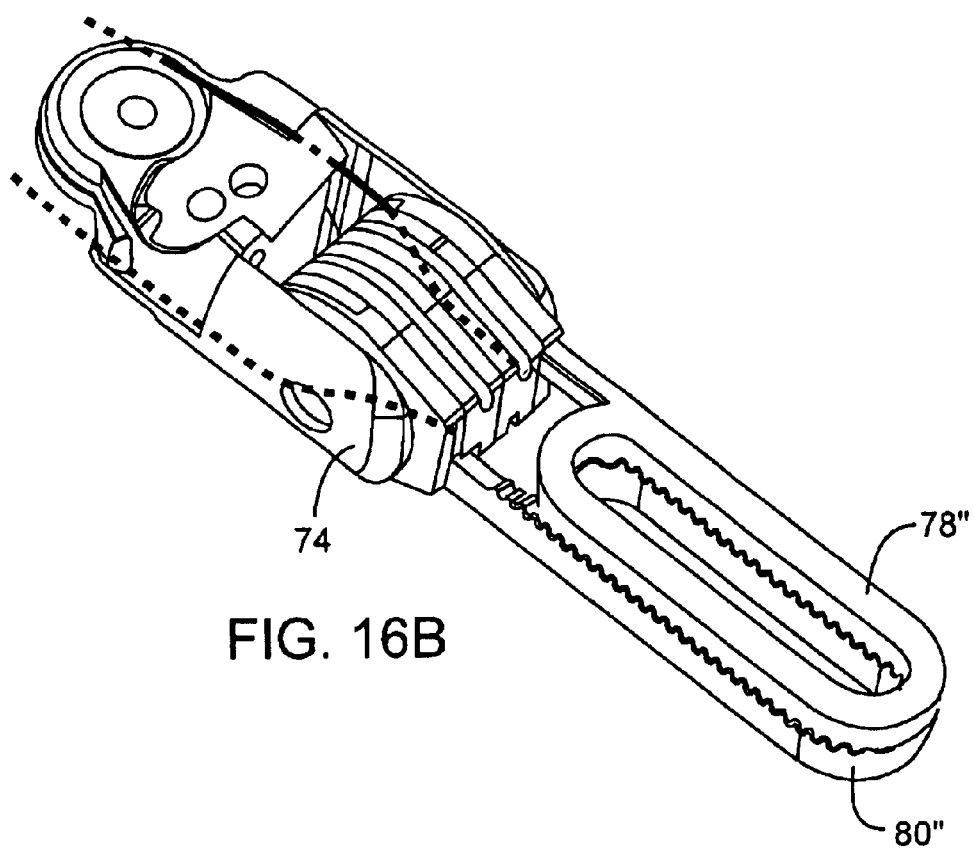
FIG. 16B illustrates the embodiment of FIG. 16A in which the end effectors are in a closed position.
Figure 16A:
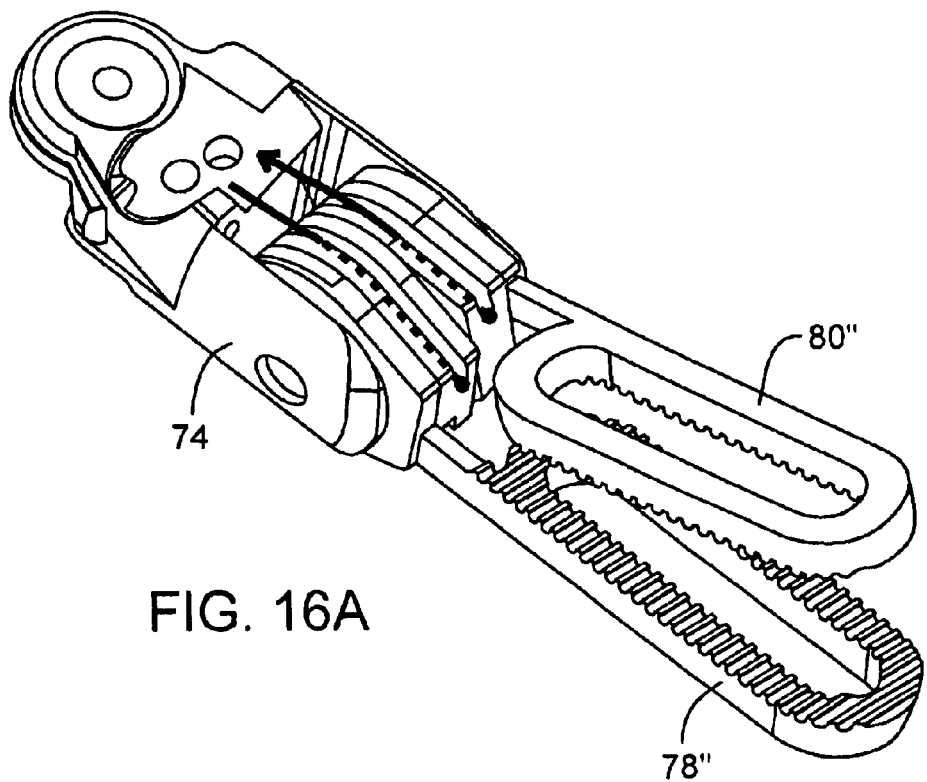
FIG. 16A illustrates an embodiment of the bipolar cauterizing instrument having conductive end effectors in which the end effectors are in an open position.

FIG. 16A and 16B illustrate yet another embodiment of the cauterizer of the present invention. In the illustrated embodiments, the bipolar cauterizer includes first and second conductive end effectors 78", 80" through which the radiofrequency current can be delivered. Similar to the above embodiments, the jaws are movable between an open (FIG. 16A) and closed configuration (FIG. 16B).

Figure 17:
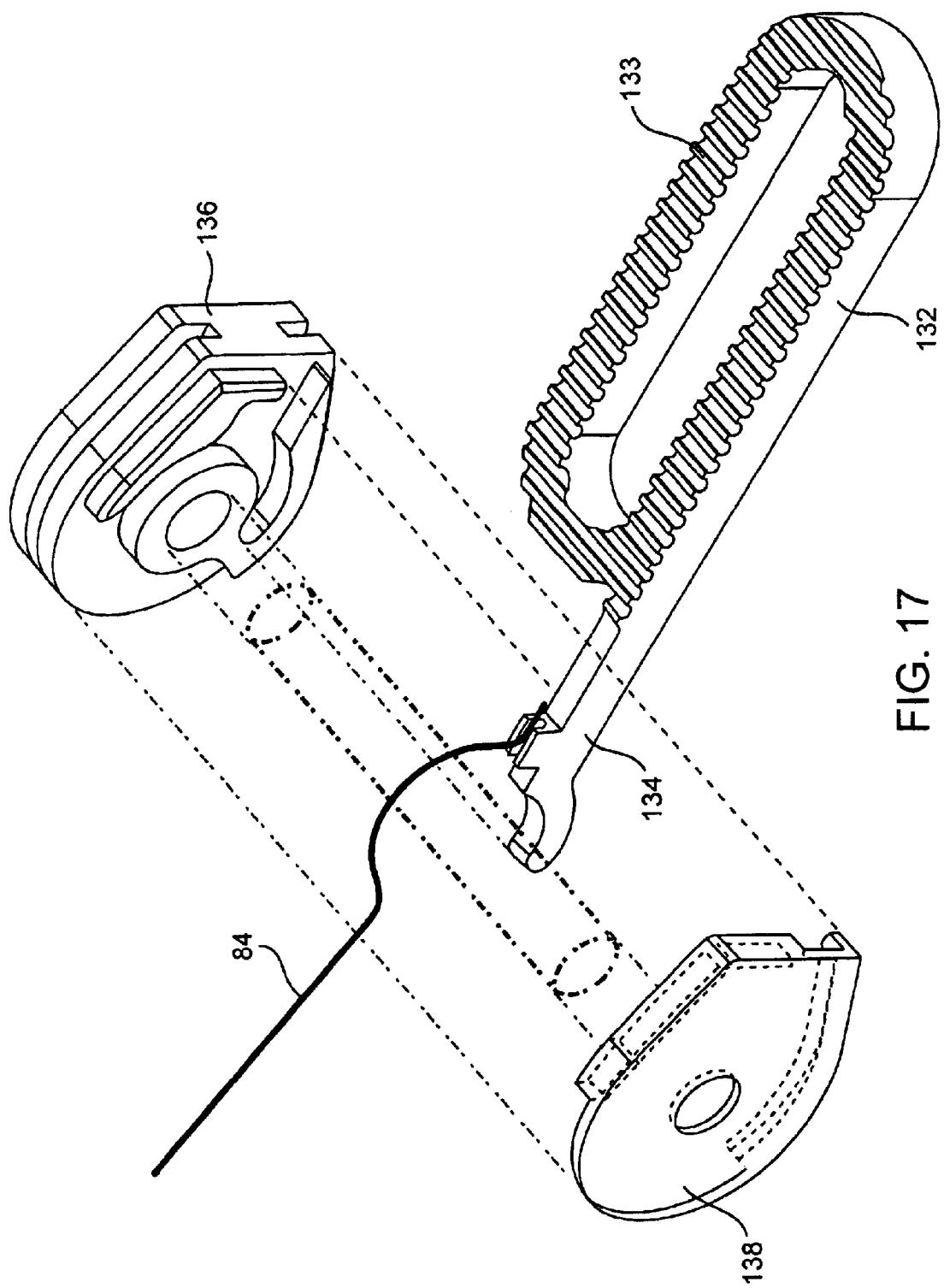
FIG. 17 is an exploded view of an end effector of FIGS. 16A and 16B.

As shown most clearly in FIG. 17, each of the end effectors include a distal jaw body 132 having grips 133 and an opening disposed in the middle of the jaw body 132. A proximal end 134 of the jaw can be electrically and mechanically connected to a conductive lead 84. Conductive leads 84 can be coupled (e.g., crimped, attached with a conductive adhesive, or the like) to a proximal portion of each of the end effectors. To prevent shorting between the end effectors 78", 80" first and second insulating pulleys 136, 138 can be disposed around each of the proximal ends 134 of the end effectors. Similar to above, while not shown, yaw cables can be coupled to the pulleys to actuate movement of the jaws.

Figure 18:
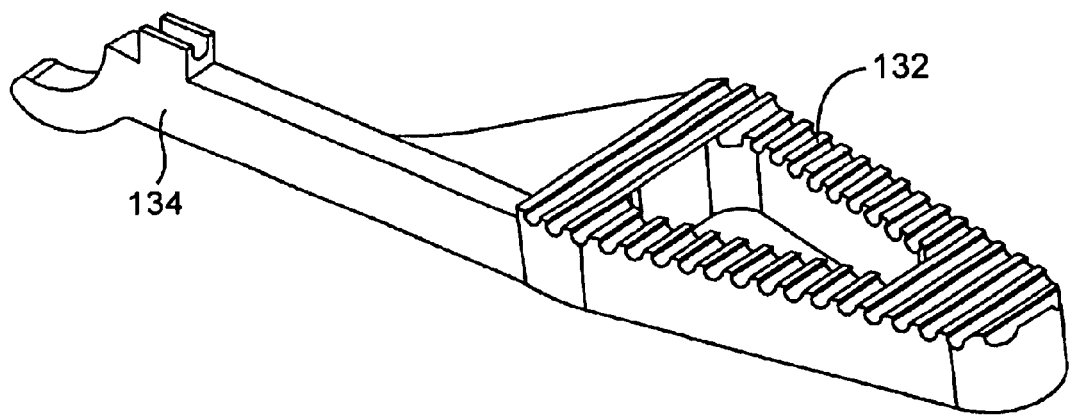
FIG. 18 is an alternative triangular shaped grip.

It should be appreciated however, that the jaws of the present invention can take a variety of shapes. Specifically, as shown in FIG. 18, the end effector can include a triangular shaped distal end 132 that has a narrower point that may allow for more finesse in grasping the target tissue. Additionally, the triangular shape more closely replicates the shape of conventional forceps.

Some exemplary methods of the present invention will now be described. As noted above, the bipolar cauterizers of the present invention are for use with a surgical robotic system. The cauterizers can be attached to a robotic arm and inserted into the patient, as described above in relation to FIGS. 1–3. The cauterizer can be moved to a target tissue and grasp the tissue with the end effectors. A high frequency energy will be delivered to electrodes disposed on the end effectors to cauterize the tissue.

As noted above, the electrodes can be provided on the end effectors in a variety of ways. In one configuration, a first end effector can have a first electrode in a groove and the second end effector can have the second electrode can be on a boss, such that when the end effectors interdigitate, the electrodes will be maintained in a spaced configuration. In another configuration, the electrodes can be disposed on nonconductive sleeves that are placed over the end effectors. Note that while the embodiments shown in FIGS. 5–8 and 16–18 are preferably operated with bipolar RF energy, alternative embodiments having the aspects of these examples may by employed with monopolar energy, wherein one of the conductive leads is connected to a ground.

While all the above is a complete description of the preferred embodiments of the inventions, various alternatives, modifications, and equivalents may be used. For example, instead of using RF energy, it is possible to couple a resistive metal lead (in an exemplary embodiment delivering a current of 4 Amps and having a voltage of approximately 6 Volts) to the wrist and end effectors to coagulate and cut the engaged tissue. In other alternative embodiments, a cutter may be incorporated on the device between the electrodes. The cutter can be stationary or spring loaded.

While not shown, the nonconductive sleeves and electrodes can have a universal interface that can snap fit or otherwise connect to the end effector of the instrument. The universal interface can be used to connect and disconnect various electrodes on the nonconductive sleeve to the conductive lead on the cauterizer so as to allow a quick disconnect of the sleeve and a quick connect of another sleeve. Thus, if the electrode configuration of the cauterizer that is inserted into the body needs to be changed, the surgeon can merely remove the cauterizer from the body, remove the sleeve and place on another nonconductive sleeve that automatically couples the electrode having a more appropriate electrode configuration, to the conductive lead on the instrument. Although the foregoing invention has been described in detail for purposes of clarity of understanding, it will be obvious that certain modifications may be practiced within the scope of the appended claims.

What is claimed is:

1. An electrosurgical instrument for use with a robotic arm, the instrument comprising:

a body comprising an interface for coupling to the robotic arm;

a wrist body that is rotatably coupled to the body about a first axis;

a pair of opposed end effectors rotatably coupled to the wrist about a second axis, wherein the pair of end effectors being movable between an open position and a closed position;

a first electrode coupled to one of the end effectors; and a second electrode coupled to one of the end effectors, wherein the first and second electrodes are in a spaced configuration when the end effectors are in the closed position.

2. The electrosurgical instrument of claim 1 further comprising an actuating device to move the pair of end effectors between the open and closed position.

3. The electrosurgical instrument of claim 2 wherein the actuating device comprises drive member(s) and pulley(s).

4. The electrosurgical instrument of claim 3 further comprising a robotic interface attached to the body for interfacing with a robotic manipulator assembly.

5. The electrosurgical instrument of claim 1 comprising first and second conductive leads that are coupleable to the first and second electrodes to a power source.

6. The electrosurgical instrument of claim 5, wherein the conductive leads extend through lumens in the body and wrist.

7. The electrosurgical instrument of claim 5 wherein first and second conductive leads electrically connect the electrosurgical power source to the electrodes, wherein at least one of the conductive leads is removably attachable to the corresponding electrode.

8. The electrosurgical instrument of claim 1 wherein the pair of end effectors comprise a corresponding pair of jaws including a corresponding pair of opposed, conductive grip surfaces, the jaws being arranged so that the respective grip surfaces are adjacent one another when the end effector is in the closed position.

9. The electrosurgical instrument of claim 8, wherein the jaws comprise a conductive material, and each jaw is coupled to the instrument by mounting to a corresponding non-conductive pulley member.

10. The electrocurgical-instrument of claim 9, wherein the jaws are replacably removably mounted from the end effectors mounted to the pulley members.

11. The electrosurgical instrument of claim 1 wherein the electrodes are substantially planar.

12. The electrosurgical instrument of claim 1 wherein the second axis is substantially orthogonal to the first axis.

13. The electrosurgical instrument of claim 1 wherein the body defines a longitudinal axis that is substantially orthogonal to the first axis, wherein the wrist and end effectors are rotatable about the longitudinal axis.

14. The electrosurgical instrument of claim 1 wherein the pair of end effectors are composed of a non-conductive material.

15. The electrosurgical instrument of claim 1 wherein the first and second electrodes are elongate.

16. The electrosurgical instrument of claim 1 wherein the electrodes in the closed position are spaced by a distance between approximately 0.01 inches and 0.10 inches.

17. The electrosurgical instrument of claim 1 wherein the first electrode is positioned within a groove and the second electrode is positioned on a boss.

18. The electrosurgical instrument of claim 1 wherein the first and second electrode are both disposed on the first end effector.

19. The electrosurgical instrument of claim 1 wherein the first and second electrodes are disposed on opposing end effectors.

20. The electrosurgical instrument of claim 1 wherein the first and second end effectors do not penetrate the tissue.

21. The electrosurgical instrument of claim 1 further comprising at least one nonconductive sleeve disposed over at least one of the end effectors, wherein at least one of the first and second electrodes are coupled to the end effectors through the nonconductive sleeves.

22. The electosurgical instrument of claim 21, wherein the sleeves are and electrodes are replacably removable from the end effectors.

23. An electrosurgical tool for use with a robotic surgery system, the tool comprising:
a body comprising a proximal portion and a distal portion, wherein the proximal portion comprises an interface for coupling to a robotic manipulator assembly;
a first and second opposing grips rotatably coupled to the distal portion of the body;
nonconductive sleeves disposed over the opposing grips;
a first and second electrode disposed on the nonconductive sleeves;
conductive leads that connect the first and second electrodes to an electrosurgical power source; and
an actuation mechanism coupled to the first and second grips to move the first and second grips between an open position and a closed position.

24. The electrosurgical tool of claim 23 wherein the grips are coupled to the body through a rotatable wrist.

25. The electrosurgical tool of claim 23 wherein the grips in the closed configuration positions the first and second electrode in a spaced configuration.

26. The electrosurgical tool of claim 25 the spaced configuration of the first and second electrode provides cauterization and cutting of a tissue engaged by the first and second grips.

27. The electrosurgical tool of claim 23 wherein the conductors are at least partially disposed outside of the body.

28. The electrosurgical tool of claim 23 wherein the electrodes are offset when the grips are in the closed position.

29. The electrosurgical tool of claim 23 wherein the actuation mechanism comprises a pulley assembly and at least one drive cable.

30. A electrosurgical cauterizer for manipulation by a robotic surgical system, the cauterizer comprising:
a body comprising an interface for coupling to a robotic surgical system;
a clevis rotatably coupled to the body about a first axis;
a first and second end effector coupled to the clevis about a second axis, wherein the first and second end effectors comprise:
a conductive grip body comprising a proximal portion and a distal portion, wherein the distal portion comprises grip for gripping a target tissue; and
nonconductive pulley disposed around the proximal portion of the grip body for insulating the first end effector from the second end effector;
a first conductive lead coupled to the first end effector and a second conductive lead coupled to the second end effector, wherein the first and second leads are attachable to a power source for delivering energy to the distal portions of the first and second end effectors.

* * * * *